United States Patent [19]
Kieval

[11] Patent Number: 5,814,079
[45] Date of Patent: Sep. 29, 1998

[54] CARDIAC ARRHYTHMIA MANAGEMENT BY APPLICATION OF ADNODAL STIMULATION FOR HYPERPOLARIZATION OF MYOCARDIAL CELLS

[75] Inventor: Robert S. Kieval, Golden Valley, Minn.

[73] Assignee: Medtronic, Inc., Minneapolis, Minn.

[21] Appl. No.: 720,886

[22] Filed: Oct. 4, 1996

[51] Int. Cl.⁶ .................................................. A61N 1/39
[52] U.S. Cl. .................................... 607/4; 607/14; 607/9
[58] Field of Search .................... 607/5, 7, 9, 11, 607/72, 14, 4

[56] References Cited

U.S. PATENT DOCUMENTS

| | | | |
|---|---|---|---|
| 4,554,922 | 11/1985 | Prystowsky | 128/419 PG |
| 4,727,877 | 3/1988 | Kallok | 128/419 D |
| 4,762,136 | 8/1988 | Baker, Jr. | 607/127 |
| 4,821,723 | 4/1989 | Baker, Jr. et al. | 128/419 D |
| 5,087,243 | 2/1992 | Avitall | 604/20 |
| 5,117,824 | 6/1992 | Keimel et al. | 128/419 D |
| 5,181,511 | 1/1993 | Nickolls et al. | 128/419 PG |
| 5,184,111 | 2/1993 | Pichl | 340/572 |
| 5,193,536 | 3/1993 | Meha | 128/419 D |
| 5,243,978 | 9/1993 | Duffin, Jr. | 607/11 |
| 5,312,441 | 5/1994 | Mader et al. | 607/5 |
| 5,314,448 | 5/1994 | Kroll | 607/5 |
| 5,334,221 | 8/1994 | Bardy | 607/14 |
| 5,366,485 | 11/1994 | Kroll et al. | 607/5 |
| 5,433,729 | 7/1995 | Adams et al. | 607/5 |
| 5,509,925 | 4/1996 | Adams et al. | |
| 5,578,062 | 11/1996 | Alt et al. | 607/5 |

FOREIGN PATENT DOCUMENTS

WO92/18198  10/1992  WIPO ................... 685/130

OTHER PUBLICATIONS

Onset & Stability for Ventricular Tachyarrythmia Detection in an Implantable Pacer Cardioversion Defibillator Computers in Cardiology Oct. 7, 1986 by Olson et al.

Automatic Tachcardia Recognition Pace by May 7, 1984 by Arzbaechert.

*Primary Examiner*—William E. Kamm
*Assistant Examiner*—Kennedy J. Schaetzle
*Attorney, Agent, or Firm*—Harold R. Patton; Michael B. Atlass

[57] ABSTRACT

An anodal stimulation method and apparatus for the prevention or treatment of tachyarrhythmias using anodal stimulation (AS) energy for effecting hyperpolarization of myocardial cells of a heart chamber to enhance the relaxation thereof in the diastolic phase and to enhance cardiac function, reverse or inhibit cell activation, and thereby treat or prevent tachyarrhythmias. In a preemptive mode with a recognizable ventricular rhythm, the AS pulse is optimally timed to be delivered in an AS delivery interval following an AS delay interval timed from a preceding ventricular depolarization to effect maximal cardiac relaxation and suppress aberrant electrical activity. In a reactive mode responsive to a detected tachyarrhythmia requiring delivery of an antitachyarrhythmia therapy, e.g. a cardioversion shock therapy, the AS pulse is delivered during charging of high voltage output capacitors providing the cardioversion shock energy. The sub-threshold AS pulse or train of pulses is increased in energy (amplitude) and/or decreased in energy to and from a peak energy level gradually rather than abruptly. The AS pulses are delivered through a plurality of discrete AS electrodes distributed about the heart chamber or through or large surface area epicardial patch or endocardial AS electrodes.

18 Claims, 8 Drawing Sheets

CARDIAC ARRHYTHMIA MANAGEMENT BY APPLICATION OF ADNODAL STIMULATION FOR HYPERPOLARIZATION OF MYOCARDIAL CELLS

CROSS-REFERENCE TO RELATED APPLICATIONS

Reference is hereby made to commonly assigned, U.S. patent application Ser. Nos.: 08/720,834 filed Oct. 3, 1996, for CARDIAC PACEMAKER PROVIDING HYPERPOLARIZATION OF CARDIAC CELLS TO ENHANCE CARDIAC FUNCTION in the name of Robert S. Kieval, VMD, Ph.D.; 08/230,578 filed Apr. 21, 1994, for TREATMENT OF ATRIAL FIBRILLATION by Luc R. Mongeon et al., now abandoned; 08/495,251 filed Jun. 27, 1995, for DEFIBRILLATION THRESHOLD REDUCTION PACING SYSTEM by Xiaoyi Min et al.; 08/230,577 filed Apr. 21, 1994, for METHOD AND APPARATUS FOR TREATMENT OF ATRIAL FIBRILLATION by William J. Combs et al., now U.S. Pat. No. 5,562,708; 08/293,769 filed Aug. 19, 1994, for ATRIAL DEFIBRILLATOR AND METHOD OF USE in the names of Xiaoyi Min et al., now U.S. Pat. No. 5,549,642; and 08/640,046 filed Apr. 30, 1996, for ATRIAL FIBRILLATION PREVENTION PACING SYSTEM by Rahul Mehra, now U.S. Pat. No. 5,683,429.

FIELD OF THE INVENTION

The present invention relates to cardiac stimulation for the prevention or treatment of tachyarrhythmias and particularly to the use of anodal stimulation (AS) energy for effecting hyperpolarization of myocardial cells of a heart chamber to enhance the relaxation thereof in the diastolic phase and to enhance cardiac function, reverse or inhibit cell activation, and thereby treat or prevent tachyarrhythmias.

BACKGROUND OF THE INVENTION

Tachyarrhythmias are episodes of inappropriate, high rate cardiac depolarizations, typically occurring in one chamber of the heart but which may be propagated from one chamber to the other, and are distinguished from sinus tachycardias that physiologically accompany exercise to provide adequate cardiac output. Tachyarrhythmias that are sufficiently high in rate and chaotic compromise cardiac output (CO) from the affected chamber(s), leading to loss of consciousness and death, in the case of ventricular fibrillation, or weakness and dizziness, in the case of atrial fibrillation or flutter and non-sinus atrial and ventricular tachycardias. Atrial fibrillation and flutter are debilitating, due to the loss of atrial contribution and interference with ventricular filling, but may not be immediately life threatening unless the episode progresses to ventricular fibrillation or stroke.

Patients suffering from tachyarrhythmias are often suitable candidates for anti-tachyarrhythmia electrical stimulation therapies applied to the heart for prevention or treatment of the tachyarrhythmias. Considerable effort has been expended in applying electrical stimulation regimens to the heart to inhibit or correct tachyarrhythmias including high rate atrial and ventricular tachycardia, fibrillation and atrial flutter. Pharmacological therapies designed to alter the cell membrane properties have also been used to prevent or treat such tachyarrhythmias. Fibrillation has generally been treated through electrical stimulation by means of high energy cardioversion/defibrillation pulses or shocks, which, in the context of implantable anti-arrhythmia devices, are applied by means of large surface area electrodes, including an electrode on or in the chamber to be defibrillated. The battery life of an implantable cardioverter-defibrillator (ICD) or pacemaker-cardioverter-defibrillator (PCD) device depends on the amount of energy expended in delivering a therapy and the delivery frequency. The high energy level employed in order to defibrillate consumes considerable energy in the range of 1.0–30.0 Joules per delivered shock. The high energy level is employed in order to simultaneously depolarize the bulk of the heart chamber to be defibrillated which includes myocardial cells in all stages of the depolarization-re-polarization cycle at the time the shock is delivered.

For patients experiencing ventricular fibrillation, the delivered cardioversion/defibrillation shock energy is necessary to save the patient's life and may not be perceived by the patient because of the loss of consciousness shortly following onset and loss of cardiac output. Episodes of atrial tachyarrhythmias occur frequently and are debilitating to the patient, even if not life threatening. Patients experiencing atrial fibrillation/flutter and some high rate ventricular tachyarrhythmias do not lose consciousness. Unfortunately, the quantity of electrical energy required to cardiovert or defibrillate the atria is sufficient, in most cases, to cause a sudden, propagated pain in the patient's chest area or to stun the patient. Typically reported defibrillation thresholds (in dogs) of $1.3\pm0.4$ Joules are required between transvenous lead bearing electrodes placed to provide atrial cardioversion pathways between the right atrium (RA) and the coronary sinus (CS) or the superior vena cava (SVC) and the CS. Other atrial electrode systems may require up to 4.0 Joules (in humans) to reliably cardiovert. Significant discomfort and often intolerable pain is associated with such atrial cardioversion/defibrillation shock therapies in this range, requiring sedation of some patients and refusal to accept the therapy by other patients.

Moreover, there is concern that the attempt to defibrillate the atria will itself induce ventricular fibrillation leading to the death of the patient. In the hospital setting, the patient is carefully monitored, and induced ventricular fibrillation may be defibrillated. However, the clinical procedure still entails enough risk that drug therapies are preferred, and atrial defibrillation is used only after other therapies fail.

The same concern has deterred the development of implantable atrial defibrillators so that patients prone to bouts of atrial fibrillation or flutter could remain ambulatory. Despite considerable effort to develop an implantable system and method to terminate or prevent atrial fibrillation or flutter, none has yet been developed commercially. One possible approach that has been widely published is to combine the atrial and ventricular fibrillation detection and cardioversion/defibrillation capabilities in a single implantable system so that induced ventricular fibrillation could be terminated. However, such a system is quite complex and expensive, both in the hardware required and in the surgical implantation procedure. Consequently, it remains a goal to provide an electrical stimulation therapy for treating atrial fibrillation/flutter and certain ventricular tachyarrhythmias that is unlikely to induce ventricular fibrillation and may be incorporated into an atrial chamber system only or that may be added to a ventricular chamber system for patient's prone to both atrial and ventricular tachyarrhythmias.

Faced with these difficulties, attempts have been made to first make the cardiac rhythm more regular so that the P-wave or R-wave may be detected and to then apply the synchronous cardioversion therapy. In commonly assigned U.S. Pat. No. 5,193,536 to Mehra, a PCD system is described where the high atrial or ventricular rate is made more regular by delivering overdrive, cathodal (negative polarity), pacing pulses to capture the heart and by using the last overdrive pacing pulse delivered as a synchronization event to time the delivery of the cardioversion shock. Another method is disclosed in U.S. Pat. No. 5,074,301 to Gill where a single pacing pulse is delivered to the atrium to allow the cardioversion shock to be delivered in the atrial refractory period.

In U.S. Pat. Nos. 5,314,448 and 5,366,485 to Kroll et al., an ICD is described having a set of cardioversion electrodes arranged around the patient's heart. When fibrillation is detected, the high output capacitors begin to be charged. As they are charged or after full charge is achieved, a "pretreatment" of the fibrillating heart muscle is commenced through the generation of a train of cathodal pulses from the voltage on the output capacitors and delivery of the pulses across the cardioversion electrodes. The capacitors are recharged and at the end of the recharge time period, the high energy cardioversion pulse is delivered across the cardioversion electrodes. It is stated that the pretreatment pulses begin the process of organizing the chaotically contracting myocardial cells and result in a reduction of cardioversion threshold and the total energy expended. It is emphasized that the pretreatment pulse voltages are well in excess of pacing level voltages and that the same cardioversion electrodes are employed to deliver the energy to the same myocardial cells as will be defibrillated by the cardioversion pulse. In this manner, the pretreatment pulses are delivered into the high current density regions of the current pathways in the heart chamber between the spaced apart cardioversion electrodes.

In the above-referenced '251 application, a method and apparatus for terminating fibrillation is disclosed using a burst of pacing energy, high frequency pulses applied into a low current density region of the cardiac tissue in the chamber in fibrillation prior to the delivery of one or more cardioversion energy pulses. The burst of pacing energy pulses is delivered between the pace/sense electrodes located in the low current density region of the cardioversion pathway around and through the heart chamber defined by the cardioversion energy distributed between the spaced apart cardioversion electrodes. The burst of pacing energy pulses injected into the low current density region results in the lowering of the cardioversion threshold, and the decreased energy cardioversion pulse effectively terminates the fibrillation episode. The burst of pacing energy pulses appears to develop a refractory island in the low energy region of the heart chamber that may itself lower the cardioversion energy, and also appears to prevent ectopic beats originating in the low energy region from fibrillating the heart.

Recently, the theoretical possibility of employing low energy pacing level pulses (i.e. less than 0.05 joules) to terminate atrial fibrillation has been explored. For example, in the recent article "Regional Control of Atrial Fibrillation by Rapid Pacing in Conscious Dogs", by Allessie et al, published in Circulation, Volume 84, No. 4, October 1991, pages 1689–1697, the ability of pacing pulses to capture a small area of fibrillating atrial tissue, if applied during a specified time interval synchronized to the sensed depolarization waveform at the pacing electrode site, is reported. However, the depolarization wavefront created by such pulses does not propagate through the entire chamber due to the varying polarization states of the tissue surrounding the stimulation site. Consequently, it has not been demonstrated that this approach can defibrillate a heart chamber actually in fibrillation.

It is generally believed that the delivery of pacing pulse bursts to the atrium can induce atrial fibrillation, unless the delivery is synchronized to P-waves to assure that the pulse bursts occur within the refractory period of the atrium. This effect is discussed in U.S. Pat. No. 5,334,221 to Bardy which discloses a device which provides pulse bursts, synchronized to a P-wave, to the SA nodal fat pad in the atrium to reduce the sinus rate of patients who suffer from angina.

Despite this general belief, it has also been proposed to avoid synchronizing the delivered pacing pulse or burst to a detected depolarization to interrupt atrial fibrillation or flutter. In the '577 application, the pacing pulses are simultaneously delivered at multiple sites distributed over a substantial portion of the atria or atrium to be treated. Rather than attempt to synchronize the delivered pulses to the high rate atrial electrogram sensed at a stimulation site, simultaneous pulse delivery at the multiple dispersed sites is intended to eventually result in capture of the atrial tissue at one or more of the stimulation sites. It is theorized that the propagation of the depolarization wavefront created in response to the delivered pacing pulse, toward cardiac tissue closely adjacent the site at which capture initially occurs, increases the probability that the adjacent tissue will be in an appropriate stage of the depolarization-repolarization cycle to be captured by the next pulse in the burst. As pulses of the burst continue to be delivered, therefore, the amount of atrial tissue captured should gradually increase, with the end result of capturing a sufficient amount of atrial tissue to terminate fibrillation.

Over the years, considerable interest has been shown in applying multiple pace/sense electrodes distributed about the heart either within the heart chamber or outside the heart chamber. In U.S. Pat. No. 4,554,922, a system is proposed for applying pacing energy pulses to a number of such electrode sites in order to either inhibit the development of or terminate a tachyarrhythmia. In U.S. Pat. No. 5,181,511, a system is disclosed for applying anti-tachycardia pacing therapies to an affected heart chamber using a "virtual electrode" approach of a multitude of electrodes arranged inside the right atrium or ventricle or on the epicardium for determining the focus site of origin of the tachycardia and for delivering the therapy in a timed fashion. The above-referenced 08/640,046 application describes a system for applying pacing pulses to a number of electrode pairs distributed about the heart. In these systems, cathodal pacing energy pulses or sub-threshold stimulation pulses are applied to the multiple electrode sites.

In these prior art attempts to treat or prevent atrial and ventricular tachyarrhythmias, the pacing pulses and pulse trains or bursts, including sub-threshold pulses and pulse bursts, are cathodal or negative polarity at delivery to the electrode in contact with the cardiac tissue. A return or anode electrode may also be in contact with the cardiac tissue or myocardium or may be remotely positioned in the patient's body such that the return path extends through other body tissue and is electrically at ground potential during delivery of the cathodal stimulation at the other electrode. Although experiments with anodal pacing pulses delivered to electrodes in contact with the heart have been undertaken in the past and are used by external pacemakers to reduce pain at the skin/electrode site of contact, direct anodal stimulation of myocardial cells to treat or prevent a tachyarrhythmia has not been, to the best of my knowledge, explored or suggested in the prior art.

SUMMARY OF THE INVENTION

Accordingly, the present invention is directed to provide a method and apparatus for effecting cardiac arrhythmia management by application of Anodal Stimulation(AS) through delivery electrodes directly to the heart or an affected heart chamber to hyperpolarize myocardial cells in the vicinity of the delivery electrodes. The arrhythmia management approaches include a preemptive treatment for reducing the incidences of tachyarrhythmia episodes and a reactive treatment for responding to detected tachyarrhythmia episodes.

In a primary preemptive treatment, the inventive apparatus and method is carried out by the means of and steps for managing tachyarrhythmias employing AS energy comprising: detecting depolarizations of a chamber of a patient's heart which may be susceptible to a tachyarrhythmia; providing a sense signal in response to a cardiac depolarization; timing an AS delivery time interval from the sense signal; generating AS energy therapies having characteristics insufficient to elicit a depolarization of myocardial cells of the heart but sufficient to effect hyperpolarization of myocardial cells; and delivering the AS pulse to the heart during AS delivery time intervals.

In a further refinement of the preemptive treatment, the delivery of the AS pulses is predicated upon determining an abnormal cardiac rhythm precurser from the sense signals, e.g., a threshold high intrinsic or unstable heart rate, etc., representing the potential onset of a more serious tachyarrhythmia.

Preferably the AS delivery time interval follows time-out of an AS time delay commencing with a sense signal to ensure application of the AS pulse waveform(s) during the intrinsic relaxation time between depolarizations of the cardiac cells of the heart.

In a particular reactive treatment, the method and apparatus of the invention is incorporated into a cardioversion system for determining the existence of a tachyarrhythmia, e.g. atrial or ventricular fibrillation, and delivering a cardioversion therapy, e.g. a defibrillation or synchronized cardioversion shock, to the affected heart chamber through large surface area cardioversion electrodes (at least one of which is in substantial contact with the heart chamber) after charging up of high voltage output capacitors. In the charging time period, AS is delivered at the large surface area cardioversion electrodes in an effort to convert the tachyarrhythmia and to reduce the cardioversion shock energy required if necessary to convert. Confirmation of the tachyarrhythmia is made following charging of the high voltage output capacitors to determine the need for the cardioversion shock energy.

In a further particular application of the invention, both the preemptive and reactive treatments are combined in a PCD system for providing comprehensive arrhythmia management of the patient's heart rate and rhythm. In any such PCD system, the delivery of the AS pulse waveform(s) is preferably made through one or more large surface area cardioversion electrode in substantial contact with the heart.

In a simpler particular application of the invention, the preemptive AS program for delivering stimulation pulses is incorporated into a pacemaker system for also providing anti-tachycardia pacing therapies in response to a confirmed tachycardia. The AS pulses may be applied as an alternative initial therapy in response to the confirmation of the tachycardia or may be the only applied therapy. The AS pulses may be delivered to one or preferably a plurality of conventional pace/sense electrodes in contact with the heart chamber being treated or through additional large surface area electrodes in substantial contact with the myocardium.

Finally, the AS pulses may be applied in the form of a sub-threshold energy pulse or a burst of pulses in a pulse train delivered for the duration of the AS delivery interval. The amplitude at the leading and/or trailing edge of the single pulse or the leading and/or trailing sub-set of pulses in the pulse train may be ramped up and/or ramped down to avoid excitation and depolarization of myocardial cells at the leading and/or trailing edges thereof. The AS pulse energy level may be altered by varying the amplitude, pulse width of the single pulse as well as the frequency or duty cycle of the pulses in the pulse train.

A number of advantages are believed to flow from the use of the method and apparatus of the present invention in an implanted system. When resting myocardial cells are hyperpolarized, the increase in membrane potential results in further relaxation, as evidenced by cell elongation, which presumably reflects a reduction in the cytosolic free calcium concentration secondary to enhanced sarcolemmal sodium-calcium exchange. In the intact heart, hyperpolarization of myocardial cells or repolarization of cells which are pathologically depolarized may also be expected to reduce cell calcium levels, either through augmented sodium-calcium exchange, or inactivation of voltage-dependent calcium channels, respectively.

Thus, I have realized that the ability to hyperpolarize large regions of myocardium could provide a method for improving myocardial relaxation and ventricular performance having the following attendant advantages. The drop in cell calcium levels accompanying hyperpolarization could help to reduce the incidence of cardiac tachyarrhythmias related to cellular calcium overload. In addition, the control of cell membrane potential by applied AS energy that hyperpolarizes the myocardium could also be a powerful method for controlling aberrant cardiac electrical activity. This approach would be very attractive as an anti-arrhythmic preemptive technique, as it could avoid the need for painful, debilitating, and potentially damaging high intensity electrical cardioversion shocks.

Moreover, even when such shocks are still required to cardiovert a heart chamber, the application of the anodal stimulation prior to the delivery is intended to relax the myocardium and make it more responsive to lower cardioversion energy shocks than would otherwise be required.

BRIEF DESCRIPTION THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein.

Figure 5A:
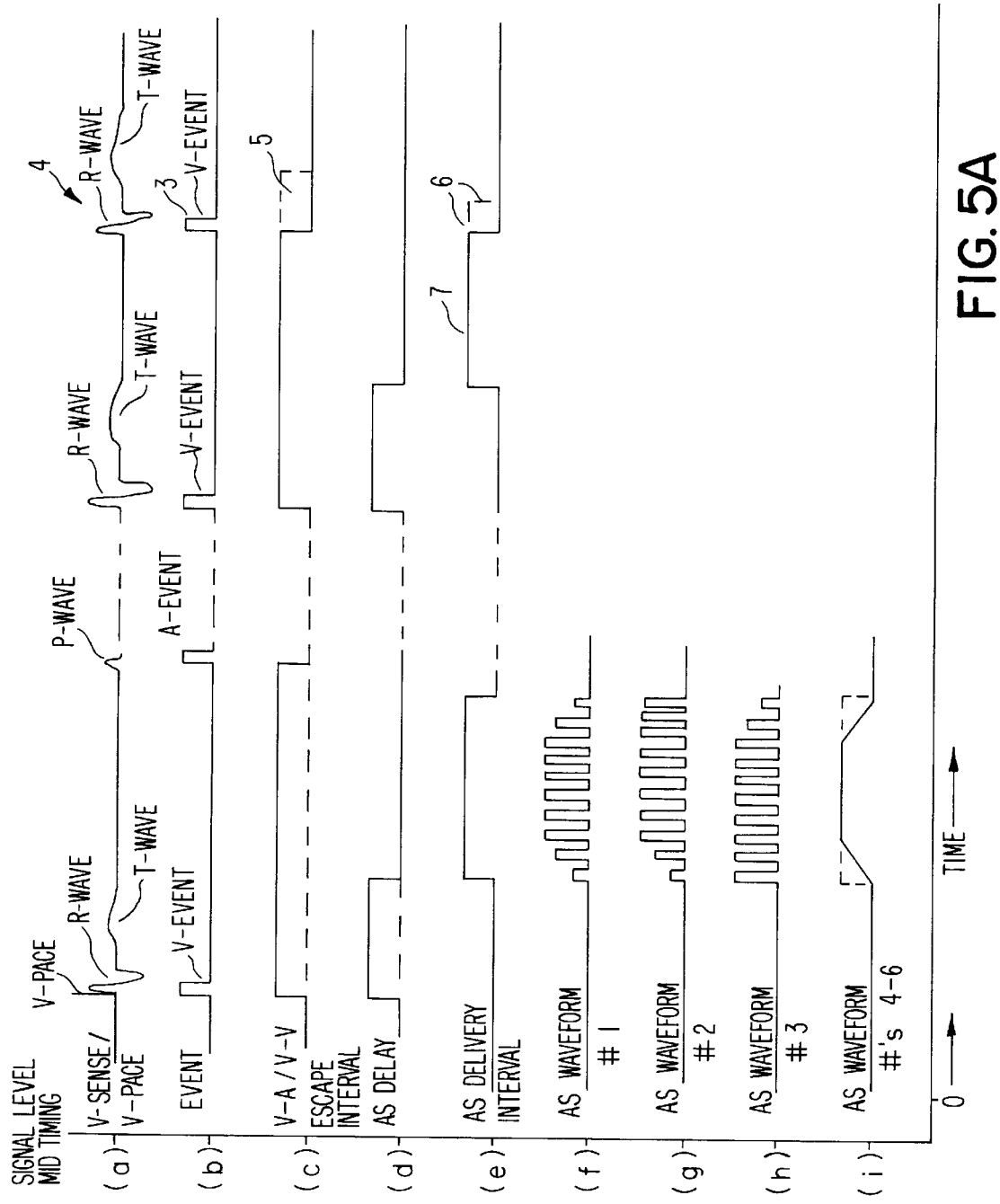
Figure 5C:
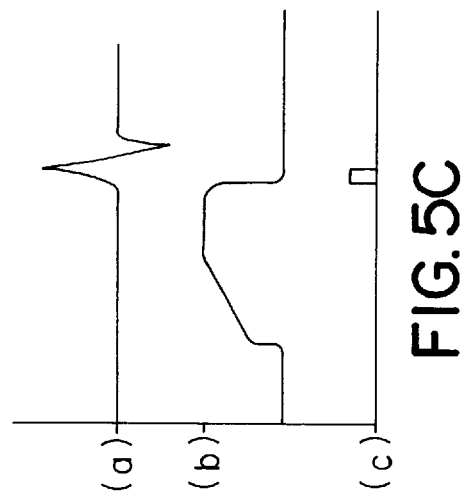
Figure 5B:
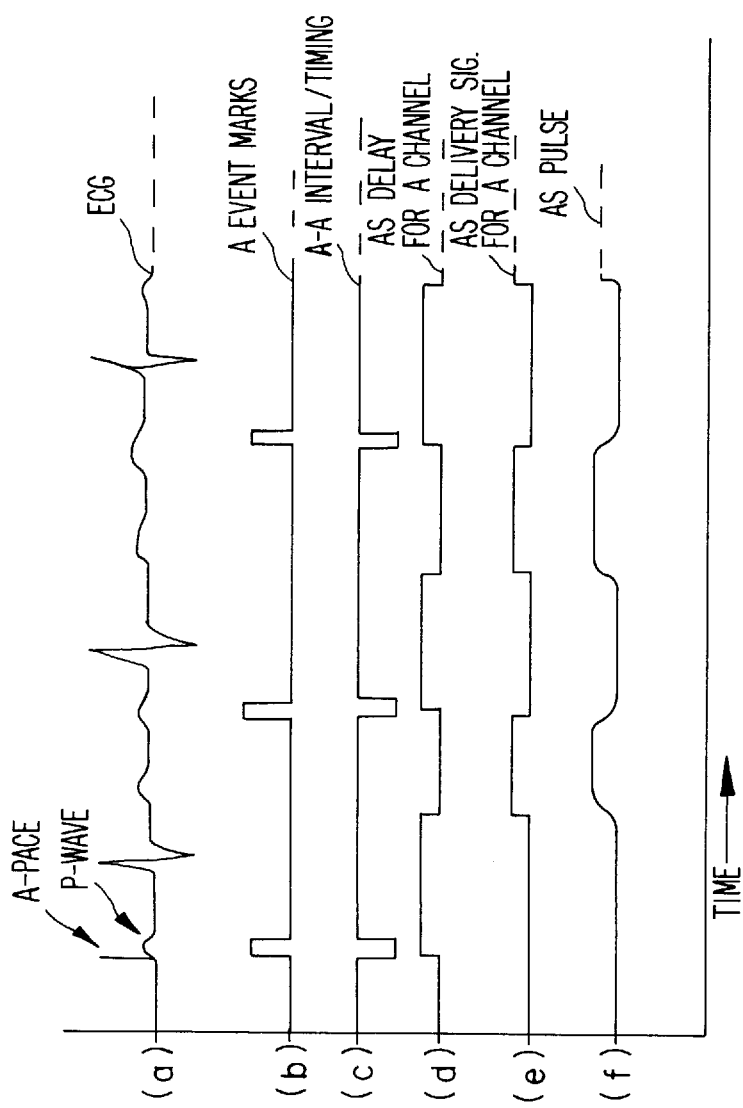

FIGS. 5A–C are an exemplary timing diagrams.

Figure 2:
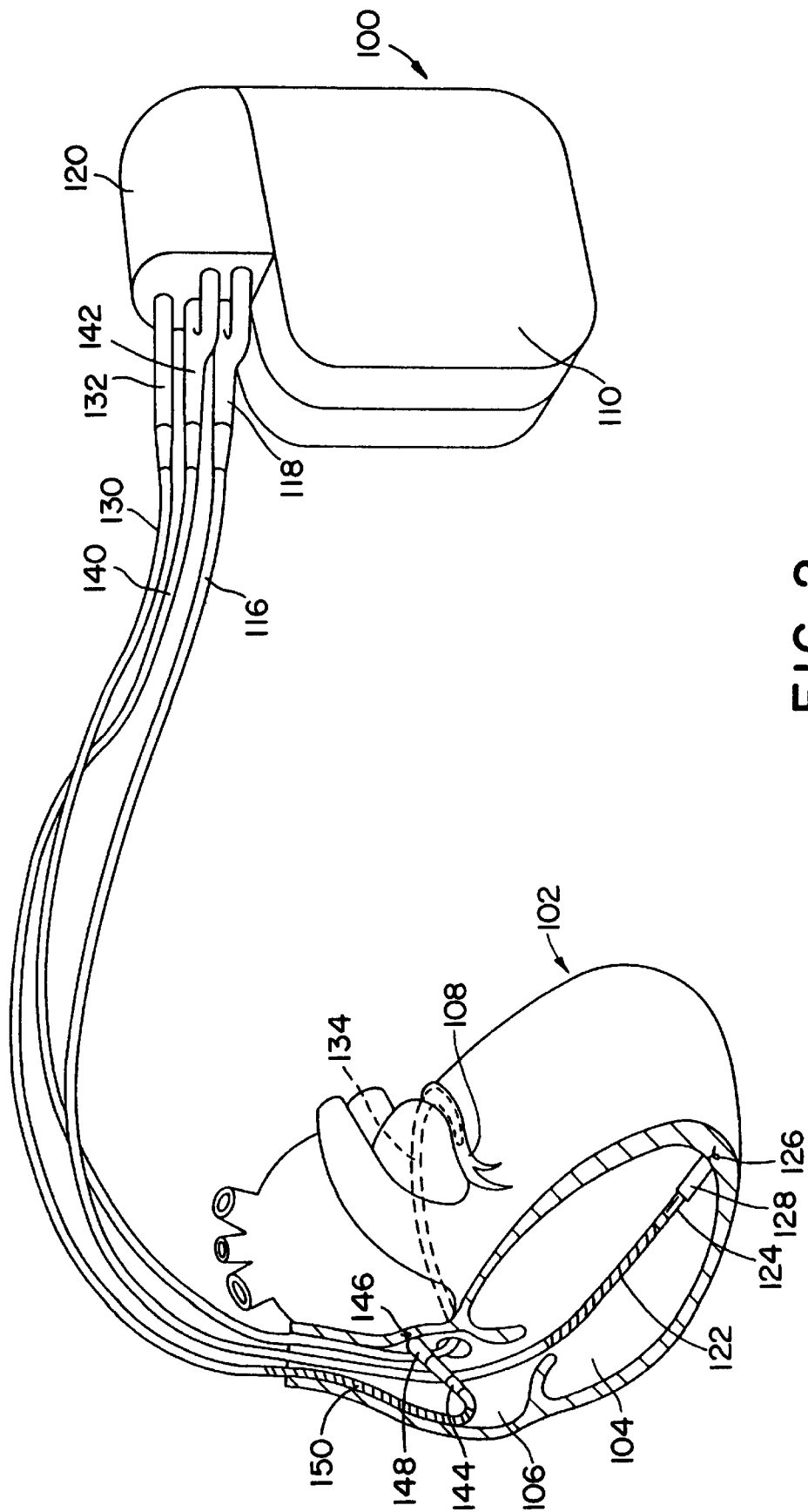
FIG. 2 is an illustration of a first embodiment of an IPG and lead system for delivering AS pulses to one or more chambers of the heart with optional back-up capabilities for providing further anti-tachyarrhythmia therapies.
Figure 3:
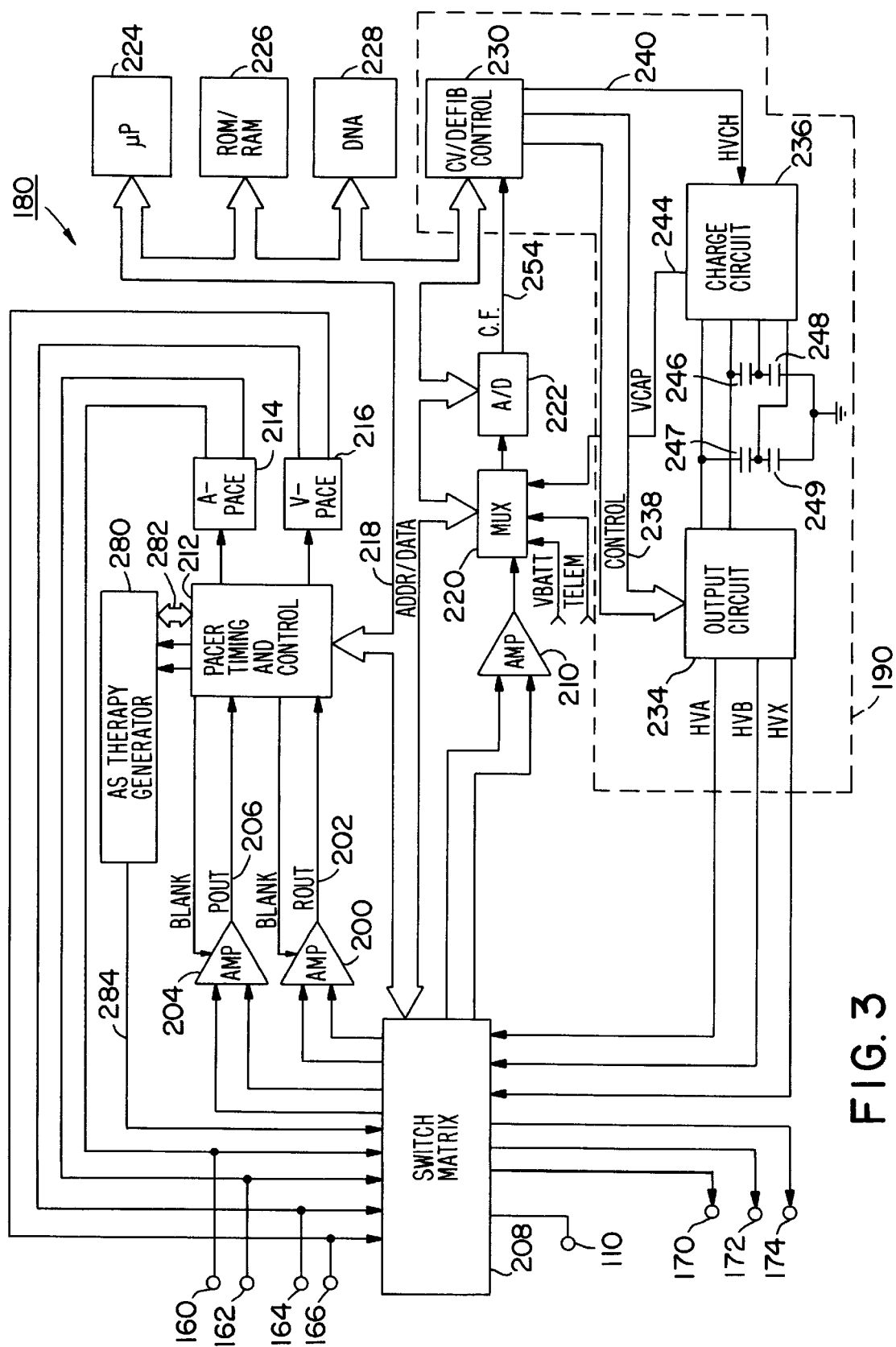
FIG. 3 is a block diagram illustrating the components of a comprehensive, atrial and ventricular, dual chamber PCD IPG system for generating and delivering AS pulses to the atria and/or ventricles which may be employed in the practice of the various embodiments of the invention.
Figure 6:
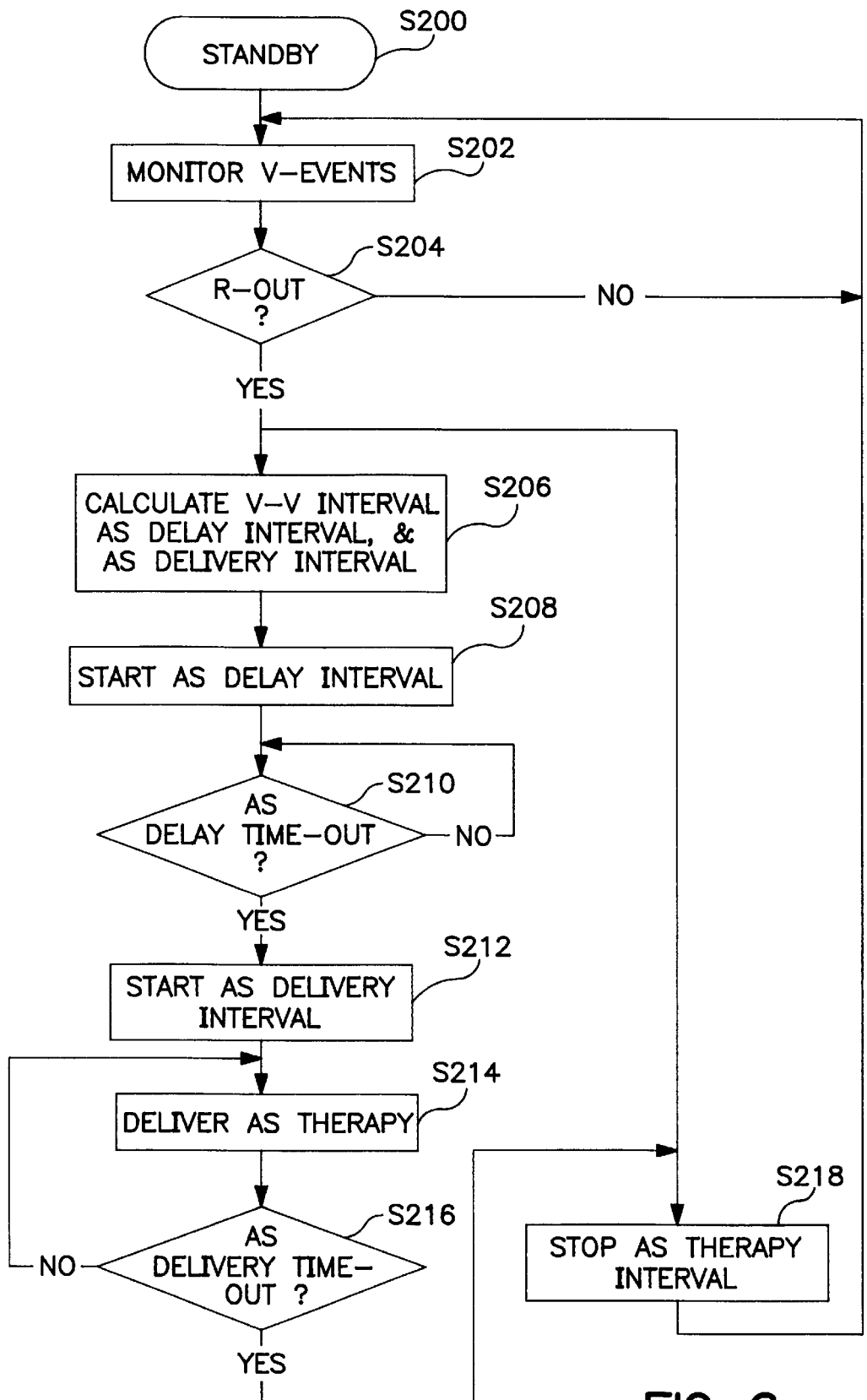
Figure 7:
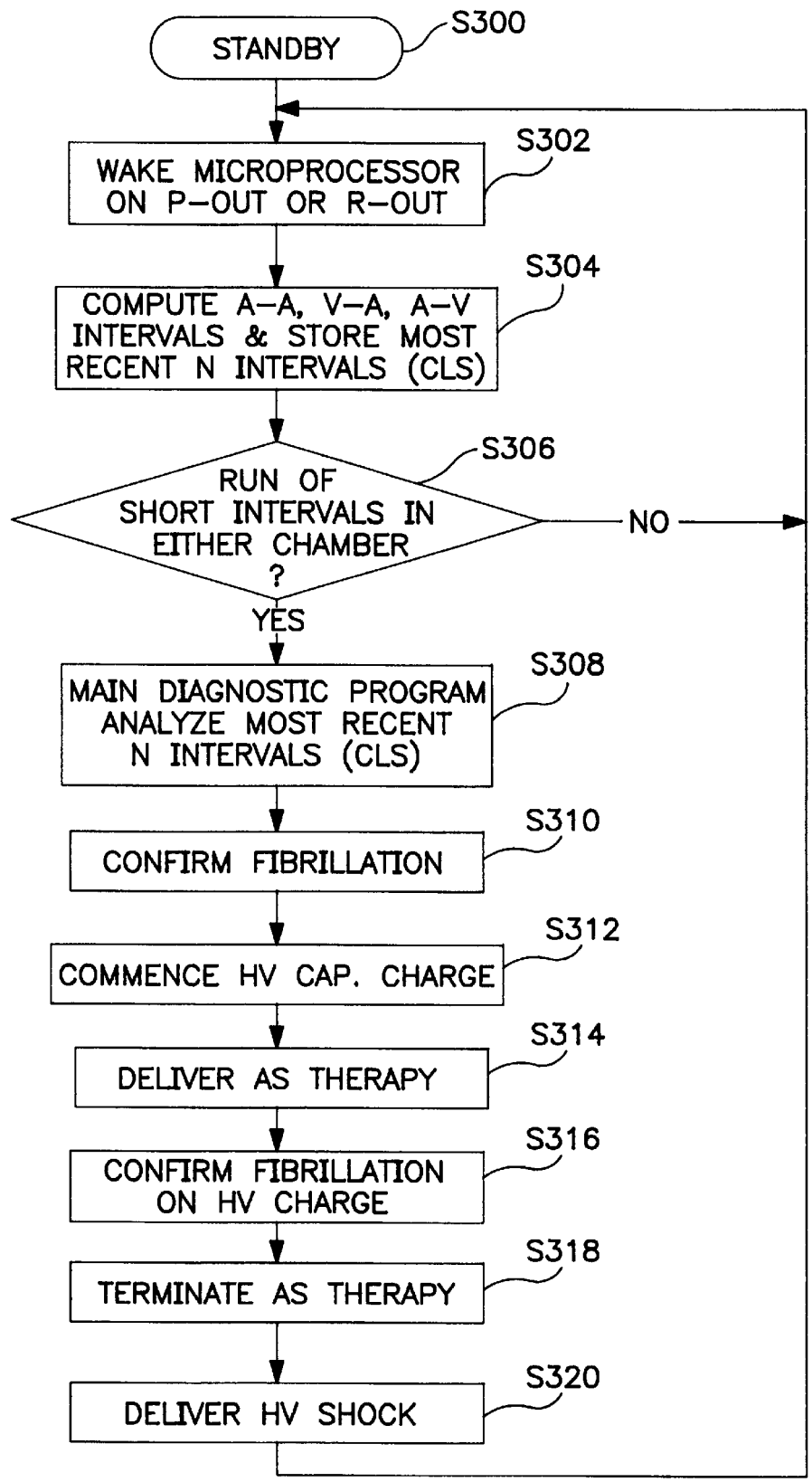

FIG. 6 is a flowchart illustrating the steps of delivering the AS in accordance with the timing diagram of FIG. 5; and FIG. 7 is a flowchart illustrating the overall steps of a second preferred embodiment of the method of practicing the present invention in responding to a tachyarrhythmia triggering delivery of a cardioversion shock therapy in response to a confirmed fibrillation, flutter or high rate ventricular tachycardia episode usable in the system of FIGS. 2 and 3.

DETAILED DESCRIPTION OF THE PREFERRED EMBODIMENTS

The preferred embodiments of the invention are explained hereafter in the context of a comprehensive implantable tachyarrhythmia management system, e.g. a PCD IPG and leads, implanted in a patient including large surface area cardioversion electrode(s) in substantial contact with the myocardium. The PCD system provides programmable single or dual chamber pacing and/or cardioversion/defibrillation capabilities of the types described in detail in commonly assigned U.S. Pat. No. 5,312,441 and the above-referenced '769 application, respectively, incorporated herein by reference in their entireties. As described below, the system may be simplified into sub-systems for operating in a single chamber or offering fewer therapies by eliminating certain of the components and operating algorithms of the comprehensive system.

Figure 1:
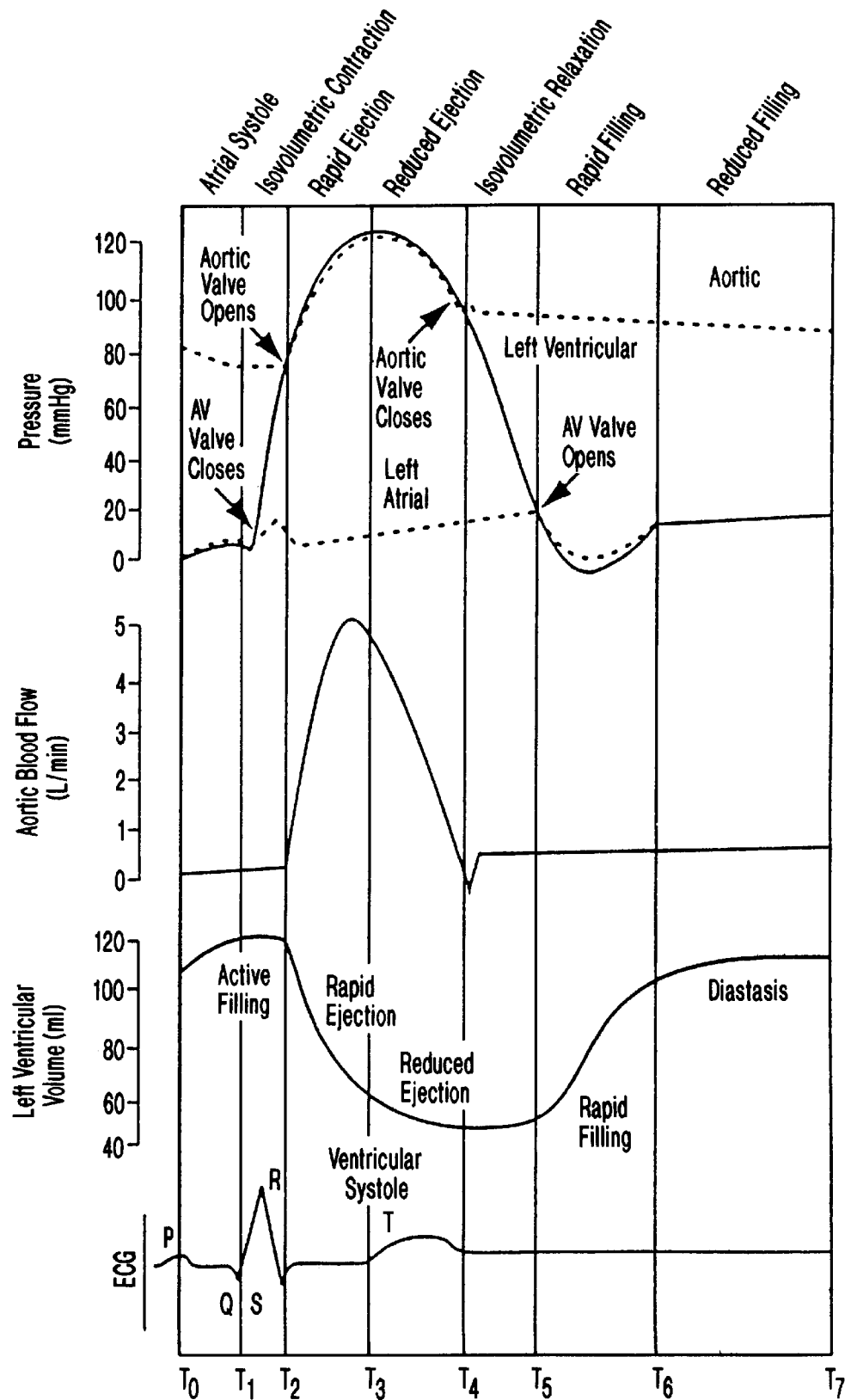
FIG. 1 is a schematic illustration of the cardiac cycle in which the delivery of an AS pulse waveform(s) is intended to be timed to be delivered within the intrinsic relaxation period between natural depolarizations, particularly in the preemptive treatment mode, to effect hyperpolarization of heart cells.

Before describing the inventive method and apparatus embodied in the preferred systems, attention is directed to FIG. 1 that depicts the electrical depolarization waves attendant a normal sinus rhythm cardiac cycle in relation to the fluctuations in absolute blood pressure, aortic blood flow and ventricular volume in the left heart. The right atria and ventricles exhibit similar pressure, flow and volume fluctuations in relation to the PQRST complex. The cardiac cycle is completed in the interval between successive PQRST complexes and following relaxation of the atria and ventricles as the right and left atria re-fill with venous blood and oxygenated blood. In sinus rhythm, the interval between depolarizations may be on the order of 500.0 ms to 1,000.0 ms for a corresponding sinus heart rate of 120 bpm to 60 bpm, respectively. In this time interval, the atria and ventricles are relaxed, and overall atrial size or volume may vary as a function of pleural pressure and respiration. In the blood pressure diagrams of FIG. 1, it may be observed that the atrial and ventricular blood pressure changes track and lag the P-waves and R-waves of the cardiac cycle. The time period $T_0$–$T_1$ encompasses the AV interval.

In patients suffering from cardiac insufficiency arising from bradycardia due to an incompetent SA node or AV-block, atrial and/or ventricular conventional pacing may be prescribed to restore a sufficient heart rate and AV synchrony. In FIG. 1, for example, atrial and/or ventricular pacing pulses would precede the P-wave and the downward Q deflection of the PQRS complex commonly referred to as the R-wave. However, CO effected by the contraction following the atrial and/or ventricular pacing pulse may be constrained by the inability of the atrial or ventricular myocardial cells to relax during the period of isovolumetric relaxation and the following periods of rapid and reduced, passive filling phase between $T_4$–$T_7$ as well as during atrial systole time period $T_0$–$T_1$ shown in FIG. 1. Thus, the amount of blood expelled from the atria and/or ventricles in the next cardiac cycle may be less than optimum. This is particularly the case with CHF patients or other patients in whom the stiffness of the heart is increased, significantly limiting cardiac filling during the passive filling phase between $T_4$–$T_7$ as well as during atrial systole time period $T_0$–$T_1$.

The relationship between the PQRST complex and the blood pressures depicted in FIG. 1 holds true for sinus rhythms with full A-V synchrony up to fairly high sinus rates providing sufficient cardiac output in physically fit individuals. When non-sinus tachycardias occur, e.g. atrial tachycardias causing the atria to "race", A-V dissociation may occur such that the ventricles continue to depolarize and contract at a lower rate and provide cardiac output with reduced atrial contribution. And in some low to medium rate ventricular tachycardias, cardiac output may be maintained at some discomfort to the patient. The present invention is directed in a first embodiment toward restoring or increasing relaxation in the period between ventricular depolarizations illustrated in FIG. 1 through the application of AS pulses to the affected heart chamber to promote the return to sinus rhythm. In one aspect of the invention, the AS delivery is triggered to a tachycardia precursor, e.g., a certain cardiac rate or instability in the cardiac cycle as evidenced by an erratic rate. In a further aspect, the AS pulse is delivered in response to the confirmation of the tachycardia or in response to atrial tachycardia and fibrillation/flutter. In a still further aspect, the hearts of such patients that are susceptible to such episodes may be continually subjected to the AS program of pulse waveforms. In all of these cases, the delivery of the AS pulses may be preferably timed to the relaxation phase of the ventricles in the presence of a relatively stable and low enough ventricular heart rate.

In a second embodiment of the invention, when an atrial or a ventricular tachyarrhythmia is detected and a cardioversion shock therapy is prescribed, e.g. in response to a sustained period of atrial fibrillation or on detection of ventricular fibrillation, timing of the delivery of the AS pulses to any recognizable portion of the cardiac cycle may be eliminated. In the case of atrial fibrillation, timing of delivery of the AS pulses (applied to the atria) to the detected ventricular rate may be continued during charge-up of the high voltage output capacitors. In the case of ventricular fibrillation, the delivery of the AS pulses to the ventricles may be continued up to the delivery of the cardioversion shock and may be resumed after delivery.

Other embodiments can be built using these concepts such that implantable devices with other then pacing or defibrillation as functions( for example, physiologic data recording and storage for use by a physician or patient, drug infusion, neurohormonal stimulation and so forth) may be used with these concepts, possibly synergistically.

To provide an explanation of how this invention can be embodied, refer to FIGS. 2 and 3 which illustrate a dual chamber, multi-programmable, PCD IPG and associated lead system for providing atrial and/or ventricular sensing functions for detecting P-waves of atrial depolarizations and/or R-waves of ventricular depolarizations, depending on the programmed operating mode, determining bradycardia, tachycardia, fibrillation and flutter, and delivering programmed therapy regimens for each in dual chamber or single chamber operating modes. FIGS. 2 and 3 are intended to provide a comprehensive illustration of different atrial and ventricular, pacing and cardioversion/defibrillation configurations that may be effected using combinations of the components thereof and several alternative operating modes and lead and electrode configurations described below and illustrated in the further drawing figures in the practice of various embodiments of the invention. Such PCD systems may be simplified or made programmable to provide atrial only, ventricular only, or both atrial and ventricular pacing modes. The pacing modes may also preferably include either or both bradycardia compensating pacing modes or antitachycardia pacing therapies. Moreover, either atrial or ventricular cardioversion/defibrillation therapies may be provided. The present invention enhances cardiac arrhythmia management using any such system triggering application of AS for hyperpolarization of myocardial cells directly to the heart or an affected heart chamber. As summarized above and described below in detail, the arrhythmia management approaches include a preemptive treatment for reducing the incidences of tachyarrhythmia episodes and a reactive treatment for responding to detected tachyarrhythmia episodes.

First, the general configuration of the comprehensive dual chamber PCD IPG and lead system will be described.

In the preferred embodiment of FIGS. 2 and 3, depending on the programmed pacing mode, pacing pulses may be applied to the atrium and/or ventricle in response to the detection of the appropriate bradycardia condition by the PCD IPG 100. The pacing and sensing functions may be effected through atrial and ventricular, bipolar tip and ring, pace/sense electrode pairs at the ends of right atrial/superior vena cava (RA) and right ventricular (RV) leads 140 and 116, respectively, fixed in the right atrium 106 and right ventricle 104, respectively, that are electrically coupled to the circuitry of IPG 100 through a connector block 120. Delivery of cardioversion or defibrillation shocks to the atrial and/or ventricular chambers of the heart 102 may be effected through selected combinations of the illustrated exemplary RA and RV cardioversion/defibrillation electrodes on the RA and RV leads and an additional coronary sinus (CS) electrode 134 on a CS lead 130 as well as an exposed surface of the outer housing or can of the IPG 100. The exposed case or "CAN" electrode 110 optionally serves as a subcutaneous cardioversion/defibrillation electrode, used as one electrode optionally in combination with one intracardiac cardioversion/defibrillation electrode for cardioverting or defibrillating either the atria or ventricles. A subcutaneous cardioversion/defibrillation electrode may be provided in addition to or substitution for the CAN electrode 110.

The RV lead 116 is depicted in a conventional configuration and includes an elongated insulated lead body, enclosing three concentric, electrically isolated, coiled wire conductors, separated from one another by tubular insulated sheaths. Located adjacent the distal end of the RV lead 116 are a pace/sense ring electrode 124, a helical, pace/sense electrode 126, mounted retractably within an insulated electrode head 128. Helical tip electrode 126 is adapted to be extended out of the electrode head 128 and screwed into the ventricular apex in a manner well known in the art. RV pace/sense electrodes 124 and 126 are each coupled to a coiled wire conductor within the RA lead body and are employed for cardiac pacing in the ventricle and for sensing near-field R-waves. RV lead 116 also supports an elongated, exposed wire coil, cardioversion/defibrillation electrode 122 (hereafter "RV COIL" electrode) a distal segment thereof adapted to be placed in the right ventricle 104 of heart 102. RV COIL electrode 122 may be fabricated from platinum, platinum alloy or other materials known to be usable in implantable cardioversion/defibrillation electrodes and may be about 5 cm in length. RV COIL electrode 122 is also coupled to one of the coiled wire conductors within the lead body of RV lead 116. At the proximal end of the lead body is a bifurcated connector end 118 having three exposed electrical connectors, each coupled to one of the coiled conductors, that are attached within the connector block 120 to connector block terminals in a manner well known in the art.

The coronary sinus (CS) lead 130 includes an elongated insulated lead body enclosing one elongated coiled wire conductor coupled to an elongated exposed coil wire cardioversion/defibrillation electrode 134. Electrode 134, illustrated in broken outline, is located within the coronary sinus and great vein 108 of the heart 100 and may be about 5 cm in length. At the proximal end of the CS lead 130 is a connector end 132 having an exposed connector coupled to the coiled wire conductor and attached within the connector block 120 to connector block terminals in a manner well known in the art.

The RA lead 140 includes an elongated lead body carrying three concentric, electrically isolated, coiled wire conductors separated from one another by tubular insulated sheaths, corresponding generally to the structure of the RV lead 116. The lead body is formed in a manner well known in the art in an atrial J-shape in order to position its distal end in the right atrial appendage. A pace/sense ring electrode 144 and an extendable helical, pace/sense electrode 146, mounted retractably within an insulated electrode head 148, are formed distally to the bend of the J-shape. Helical tip electrode 146 is adapted to be extended out of the electrode head 148 and screwed into the atrial appendage in a manner well known in the art. RA pace/sense electrodes 144 and 146 are employed for atrial pacing and for near-field sensing of P-waves. An elongated, exposed cardioversion/defibrillation RA/SVC COIL electrode 150 is supported on RA lead 140 extending proximally to pace/sense ring electrode 144 and coupled to the third coiled wire conductor within the RA lead body. RA/SVC COIL electrode 150 preferably is 10 cm in length or greater and is configured to extend from within the SVC and toward the tricuspid valve. At the proximal end of the RA lead 15 is a bifurcated connector 13 which carries three exposed electrical connectors, each coupled to one of the coiled wire conductors, that are attached within the connector block 120 to connector block terminals in a manner well known in the art.

The circuitry within IPG 100 communicates with an external programmer (not shown) through an RF communication link in a manner well known in the art. A lead integrity test may be initiated by commands from the external programmer in a manner well known in the art, to select lead conductor pairs and collect impedance data for analysis as described in detail below. In addition, in accordance with the present invention, the circuitry may initiate a lead integrity test sequence automatically on a periodic basis, e.g. when the patient is expected to be sleeping, to obtain such lead data for transmission out of the IPG 100 upon interrogation at a later time.

The PCD system configuration and operating modes may be varied by eliminating: (1) the atrial or ventricular pacing capability including the associated pace/sense electrodes thereby providing dual chamber cardioversion/defibrillation and single chamber bradycardia/tachycardia pacing capabilities; (2) in a single chamber PCD, the atrial or ventricular pacing and sensing capability along with the corresponding chamber cardioversion/defibrillation capability and associated leads and electrodes; (3) single chamber, atrial or ventricular, cardioversion/defibrillation capability and associated leads/electrodes while retaining the dual chamber pacing and sensing capability thereby providing single chamber cardioversion/defibrillation and dual chamber bradycardia/tachycardia pacing capabilities; (4) in a special case of an atrial PCD, the ventricular cardioversion/ defibrillation capability while retaining at least the atrial sense capability and the ventricular sense capability for providing R-wave synchronization of the delivered atrial cardioversion therapies; (5) in a pacing only configuration, providing only anti-tachycardia pacing therapies in either or both the atrial and ventricular chambers. The application of the preemptive and reactive AS pulses of the present invention is preferably effected through whichever of the large surface area, intracardiac electrodes 122, 134 and/or 150, that are substantially in contact with the myocardium as shown in FIG. 2, is present in the particular configuration, employing the CAN electrode 110 as the return electrode. Moreover, as illustrated below, other large surface area electrodes, including epicardial patch electrodes, may be used in the system in addition to or substitution for any one of the electrodes 122, 134, 150 depicted in FIG. 2. Furthermore, adjunct systems which may synergistically combine other therapies such as drug delivery or neurohormonal stimulation may be included.

Finally, in a further simplification, the present invention may be practiced to provide the preemptive or reactive AS program in substitution for any or all of the atrial and/or ventricular anti-tachyarrhythmia pacing and/or cardioversion/defibrillation therapies described below in reference to FIG. 3. In such an embodiment, the AS pulse may be delivered through large surface area intracardiac or epicardial patch electrodes in substantial contact with the myocardium of the heart chamber to be treated. Alternatively or additionally, the AS pulses may be delivered to the pace/sense electrodes in contact with the myocardium, relying upon the virtual electrode to affect a mass of myocardial cells sufficiently large to interrupt or favorably modify the aberrant depolarization waves provoking or maintaining the tachyarrhythmia.

Turning to FIG. 3, it is a functional schematic diagram of the circuitry 180 of a comprehensive dual chamber, implantable PCD 100 which may be used to support the practice of the present invention. Certain of the pace/sense and cardioversion/defibrillation functions may be disabled or not provided to configure the PCD device to operate in subcombinations of dual chamber or single chamber PCD operating modes including at least the above-described modes. Therefore, FIG. 3 should be taken as exemplary of the circuitry 180 of the type of PCD IPG 100 in which the invention may be embodied, and not as limiting, as it is believed that the invention may usefully be practiced in a wide variety of device implementations.

The PCD IPG circuitry of FIG. 3 includes a high voltage section 190 for providing relatively high voltage cardioversion/defibrillation shocks when needed in response to detection of a tachyarrhythmia and a low voltage pace/ sense section for sensing P-waves and/or R-waves and providing relatively low voltage bradycardia pacing and anti-tachycardia pacing therapies. In accordance with this embodiment of the present invention, the low voltage section including a further The AS system's pulse generator 280 for generating the AS pulses in response to or anticipation of a tachyarrhythmia controlled by the pacer timing and control (PTC) circuitry 212. Other functions, including uplink and downlink telemetry with an external programmer for interrogating or programming operating modes and parameters, are also provided in a manner well known in the art. All of the circuit blocks are operated under the control of a microcomputer including a microprocessor 224, ROM/ RAM 226 and DMA 228.

The block diagram of FIG. 3 depicts the atrial and ventricular pace/sense and cardioversion/defibrillation lead connector terminals of the connector block 120 of FIG. 2. Assuming the electrode configuration of FIG. 2, the correspondence to the illustrated leads and electrodes is as follows: Optional CAN electrode 110 can be accessed through switch matrix and protection circuit 208 to operate as a cardioversion/defibrillation electrode and separately as the return electrode when AS pulses are delivered to the other selected electrodes through connections made in switch matrix and protection circuit 208. Terminal 174 is adapted to be coupled to the CV lead connector 132 and to CV electrode 134 or to a subcutaneous patch electrode. Terminal 172 is adapted to be coupled through RV lead 116 to RV COIL electrode 122. Terminal 170 is adapted to be coupled through RA lead 140 to RA/SVC COIL electrode 150. However, it will be understood that fewer terminals may be provided than depicted, and/or that one or more differing cardioversion/ defibrillation leads, e.g. epicardial patch electrode and subcutaneous patch electrode bearing leads may also be employed for one or more of the depicted cardioversion/defibrillation electrode bearing leads.

Terminals 164 and 166 are adapted to be coupled through lead 116 to RV pace/sense electrodes 124 and 126 for sensing and pacing in the ventricle. Terminals 160 and 162 are adapted to be coupled through lead 140 to RA pace/sense electrodes 144 and 146 for sensing and pacing in the atrium. In one embodiment, bipolar pace/sense electrodes are employed in the practice of the invention, but their configuration, fixation in contact with and positioning with respect to the atria and ventricles may differ from those shown in FIG. 1.

Terminals 170, 172, 174 and/or CAN electrode 110 are adapted to be coupled to high voltage output circuit 234 through connections made in switch matrix under control of signals received on address/data bus 218 from microprocessor 224. High voltage output circuit 234 includes high voltage switches controlled by CV/DEFIB CONTROL logic 230 via control bus 238. The switches within circuit 234 control which electrodes are employed and which are coupled to the positive and negative terminals of the capacitor bank including a first capacitor pair 246 and 248 and a second capacitor pair 247 and 249 during delivery of the intermediate and high voltage cardioversion and defibrillation shocks. Preferably biphasic shocks are generated in "A" and "B" phases in a manner disclosed in the '441 patent and in commonly assigned U.S. Pat. No. 5,163,427 wherein an implantable cardioverter/defibrillator system which is capable of providing three defibrillation shock methods, with a minimum of control and switching circuitry, is disclosed. The output stage is provided with the two separate output capacitor banks 246, 248 and 247, 249 which are sequentially discharged during sequential shock defibrillation and simultaneously discharged during single or simultaneous shock defibrillation through a two or three defibrillation electrode system. Other cardioversion shock wave shapes have been proposed in conjunction with a variety of electrode systems in order to achieve more efficient cardioversion, including bi-phasic or multi-phasic wave form shocks generated in rapid sequence and applied to the same or separate electrode systems. Despite the additional complexity, it is expected that cardioversion may be achieved more rapidly after the onset of an arrhythmia and at lower current consumption. In order to achieve low current consumption, these stimulation therapy regimens require rapid and efficient charging of high voltage output capacitors 246–249 from low voltage battery power sources as well as efficient sequential (or simultaneous) discharge of the capacitors through the electrode systems employed.

Terminals 164 and 166 are coupled through switch matrix and protection circuit 208 to the R-wave sense amplifier 200 through an input isolation circuit 201. R-wave sense amplifier 200 preferably takes the form of an automatic gain controlled amplifier providing an adjustable sensing threshold as a function of the measured R-wave signal amplitude. A R-OUT signal is generated on line 202 whenever the signal sensed between the VTIP and VRING electrodes appearing at terminals 164 and 166 exceeds the current ventricular sensing threshold. Terminals 160 and 162 are similarly coupled through switch matrix and protection circuit 208 through an input isolation circuit 203 to the P-wave sense amplifier 204, which preferably also takes the form of an automatic gain controlled amplifier providing an adjustable sensing threshold as a function of the measured P-wave amplitude. A P-OUT signal is generated on line 206 whenever the signal sensed between ATIP, ARING electrodes coupled to terminals 160, 162 exceeds the current atrial sensing threshold. The APACE and VPACE output circuits 214 and 216 are also coupled (through certain components described below in reference to FIG. 5 and not shown in FIG. 2) to terminals 160, 162 and 164, 166, respectively. The atrial and ventricular sense amplifiers 204 and 206 are isolated from the APACE and VPACE output circuits 214 and 216 by appropriate isolation and blanking circuitry in each sense amplifier 204, 200 and the associated input isolation circuits 203, 201 operated by A-BLANK and V-BLANK signals during and for a short time following delivery of a pacing pulse in a manner well known in the art. The general operation of the R-wave and P-wave sense amplifiers 200 and 204 may correspond to that disclosed in U.S. Pat. No. 5,117,824, incorporated herein by reference in its entirety.

Switch matrix and protection circuit 208 is also used in an EGM sensing mode to select which of the available pace/sense electrodes are coupled to wide band (0.5–200 Hz) EGM sense amplifier 210 for use in digital signal storage and analysis of the patient's atrial and ventricular EGM. The selection of the terminals 160, 162 and 164, 166 is controlled by the microprocessor 224, via data/address bus 218, in order to apply atrial and ventricular signals to the bandpass amplifier 210. Alternatively, far field EGM signals may be measured by substituting the IPG CAN electrode 110 for one of the atrial and ventricular pace/sense electrodes coupled to the atrial and ventricular pace/sense terminals 160, 162 and 164, 166. In either case, output signals from bandpass amplifier 210 are provided to multiplexor 220, and thereafter converted to multi-bit digital signals by A/D converter 222, for storage in RAM in ROM/RAM 226 under control of DMA 228. Microprocessor 224 may employ digital signal analysis techniques to characterize the digitized signals stored in ROM/RAM 226 to recognize and classify the patient's heart rhythm employing any of the numerous signal processing methodologies known to the art.

The PCD IPG circuitry of FIG. 3 provides atrial and/or ventricular cardiac pacing for bradycardia and tachycardia conditions and synchronized cardioversion and defibrillation shock therapies for tachyarrhythmias in accordance with therapy regimes programmed by the physician. With respect to the pacing operations, the PTC circuitry 212 can include programmable digital counters which control the basic time intervals associated with bradycardia pacing modes including DDD, VVI, DVI, VDD, AAI, DDI and other modes of single and dual chamber pacing well known to the art. PTC circuitry 212 also controls escape intervals associated with timing and delivering anti-tachyarrhythmia pacing in both the atrium and the ventricle, employing any anti-tachyarrhythmia pacing therapies known to the art. In the process, PTC circuitry 212 also times the operation of and processes P-OUT and R-OUT sense events of the atrial and ventricular sense amplifiers 204 and 200.

In normal pacing modes of operation, intervals defined by PTC circuitry 212 include atrial and ventricular pacing escape intervals, blanking intervals, the refractory periods during which sensed P-waves and R-waves are ineffective to restart timing of the escape intervals, and the pulse widths of the pacing pulses. These intervals are determined by microprocessor 224, in response to stored data in RAM in ROM/RAM 226 and are communicated to the PTC circuitry 212 via address/data bus 218. PTC circuitry 212 also determines the amplitude of the cardiac pacing pulses under control of microprocessor 224. Other combinations of circuits cdan, of course, be used to provide these functions, if desired.

During bradycardia pacing, the escape interval counters within PTC circuitry 212 are reset upon sensing of R-waves and P-waves as indicated by a signals on lines 202 and 206. In accordance with the selected pacing mode, PTC circuitry 212 triggers generation of atrial and/or ventricular pacing pulses by APACE and VPACE output circuits 214 and 216 on time-out of the appropriate escape interval counters. The pacing escape interval counters are also reset on generation of pacing pulses, and thereby control the basic timing of cardiac pacing functions.

Isolation circuits 203 and 201 operate to disconnect the input terminals of atrial and ventricular sense amplifiers 204 and 200 from the APACE and VPACE output circuits 214 and 216 on time-out of the atrial and ventricular escape intervals for a short time under the control of the PTC circuitry 212 in a manner well known in the art. Blanking of the atrial and ventricular sense amplifiers 204 and 200 is also provided by PTC circuitry 212 in accordance with the conventional practice. Although not shown in FIG. 3, it will be understood that high voltage protection power FETs are incorporated within switch matrix and protection circuit 208 between the atrial and ventricular pace/sense terminals, 160, 162 and 164, 166 and the APACE and VPACE output circuits 214 and 216, respectively, to protect against IC damage from cardioversion/defibrillation shock energy induced across the electrodes of the pace/sense leads when such shocks are delivered.

With respect to anti-tachyarrhythmia pacing, the value of the counts present in the escape interval counters when reset by sensed R-waves and P-waves may be used as measures of the durations of R-R intervals, P-P intervals, P-R intervals and R-P intervals, which measurements are stored in RAM in ROM/RAM 226 and used to detect the presence of tachyarrhythmias as described below. Microprocessor 224 operates as an interrupt driven device, and is responsive to interrupts from PTC circuitry 212 corresponding to the occurrence of sensed P-waves (P-OUT) and R-waves (R-OUT) and corresponding to the generation of cardiac pacing pulses. These interrupts are provided via data/address bus 218. Any necessary mathematical calculations to be performed by microprocessor 224 and any updating of the values or intervals controlled by PTC circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, a portion of RAM in the ROM/RAM 226 (FIG. 3) is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. Appropriate ventricular tachyarrhythmia detection methodologies measuring such factors are described in the article "Onset and Stability for Ventricular Tachyarrhythmia Detection in an Implantable Pacer-Cardioverter-Defibrillator" by Olson et al., published in *Computers in Cardiology*, Oct. 7–10, 1986, IEEE Computer Society Press, pages 167–170, incorporated herein in its entirety. Appropriate atrial tachycardia, fibrillation and flutter detection methodologies are disclosed in the article "Automatic Tachycardia Recognition", by Arzbaecher et al., published in *PACE*, Vol. 7, May–June 1984, part II, pages 541–547 and in PCT Application Ser. No. U.S. 92/02829, Publication No. WO 92/18198 by Adams et al., both incorporated herein by reference in their entireties. In the PCT application, careful synchronization of the high voltage atrial defibrillation shock to the ventricles to avoid induction of ventricular tachycardia or fibrillation is also discussed.

In the event that an atrial or ventricular tachyarrhythmia is detected, and an anti-tachyarrhythmia pacing regimen is prescribed, appropriate timing intervals for controlling generation of anti-tachyarrhythmia pacing therapies are loaded from microprocessor 224 into the PTC circuitry 212, to control the operation of the escape interval counters therein and to define refractory periods during which detection of R-waves and P-waves is ineffective to restart the escape interval counters.

In the event that generation of a cardioversion or defibrillation shock is required, microprocessor 224 employs an escape interval counter to control timing of such cardioversion and defibrillation shocks, as well as associated refractory periods. In response to the detection of atrial or ventricular fibrillation or tachyarrhythmia requiring a cardioversion shock, microprocessor 224 activates cardioversion/defibrillation control circuitry 230, which initiates charging of the high voltage capacitors 246 and 248 via charging circuit 236, under control of high voltage charging control line 240. The voltage on the high voltage capacitors 246–249 is monitored via VCAP line 244, which is passed through multiplexor 220. In response to reaching a predetermined value set by microprocessor 224, the voltage on VCAP line 244 results in generation of a logic signal on Cap Full (CF) line 254, terminating charging. Thereafter, timing of the delivery of the defibrillation or cardioversion shock is controlled by PTC circuitry 212. Following delivery of the shock therapy, the microprocessor 224 then returns the operating mode to cardiac pacing and awaits the next successive interrupt due to pacing or the occurrence of a sensed atrial or ventricular depolarization.

In the illustrated operating system, delivery of the cardioversion or defibrillation shocks is accomplished by output circuit 234, under control of control circuitry 230 via control bus 238. Output circuit 234 determines whether a monophasic or biphasic shock is delivered, the polarity of the electrodes and which electrodes are involved in delivery of the shock. Output circuit 234 also includes high voltage switches which control whether electrodes are coupled together during delivery of the shock. Alternatively, electrodes intended to be coupled together during the shock may simply be permanently coupled to one another, either exterior to or interior of the device housing, and polarity may similarly be pre-set, as in current implantable defibrillators. An example of output circuitry for delivery of biphasic shock regimens to multiple electrode systems may be found in U.S. Pat. No. 4,727,877, incorporated by reference in its entirety.

In modern implantable PCD IPGs, the particular therapies are programmed in during a patient work up by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On re-detection of tachycardia, a more aggressive anti-tachycardia pacing therapy may be scheduled. If repeated attempts at anti-tachycardia pacing therapies fail, a higher level cardioversion shock may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion shocks if the rate of the detected tachycardia is above a preset threshold. The references cited above in conjunction with descriptions of prior art tachycardia detection and treatment therapies are applicable here as well.

In the event that atrial or ventricular fibrillation is identified, the typical therapy will be delivery of a high amplitude defibrillation shock, typically in excess of 10.0 joules in the case of ventricular fibrillation and about 5.0 joules or less in the case of atrial defibrillation. Lower energy levels will be employed for cardioversion. As in the case of currently available implantable pacemakers/cardioverter/defibrillators, and as discussed in the above-cited references, it is envisioned that the amplitude of the defibrillation shock may be incremented in response to failure of an initial shock or shocks to terminate fibrillation.

The criteria for detection of a tachyarrhythmia and the particular selection of the cardioversion/defibrillation terminals and associated cardioversion/defibrillation electrodes for delivery of the physician prescribed therapies are not of primary importance in the practice of the present invention. Nor are any prescribed anti-tachyarrhythmia therapies necessary for the practice certain embodiments of the present invention. The methods of the first embodiment of the present invention may be practiced in a system that does not necessarily include a high voltage circuit 190. The methods of the second embodiment are practiced when the high voltage (HV) charge circuit 236 is being operated in response to a detected tachyarrhythmia and when cardioversion/defibrillation therapies are about to be delivered if the presence of the tachyarrhythmia is confirmed when the charging process is completed.

Turning to the generation and delivery of AS pulses of the present invention, the AS system pulse generator 280 is operated under the control of timing and control signals received on AS characteristics bus 282 from the PTC circuitry 212. The PTC circuitry 212 is operated in turn by commands received on bus 218 from the microcomputer 224. The electrodes to be employed in the delivery of the AS pulses is determined by control signals supplied by microcomputer 224 on bus 218 to switch matrix and protection circuit 208. The switches in switch matrix and protection circuit 208 protect the AS system pulse generator 280 from damage by cardioversion shock energy applied to the same electrodes. The AS operating modes, tachyarrhythmia detection or anticipation criteria for triggering delivery of preemptive or reactive AS pulses, the selection of electrodes to be employed, the type of AS system pulses or programs of pulses to be applied, the timing of delivery of the AS pulses, and the like, can be made programmable by the physician, the programmed in parameter values and modes stored in RAM in ROM/RAM 226.

Figure 4:
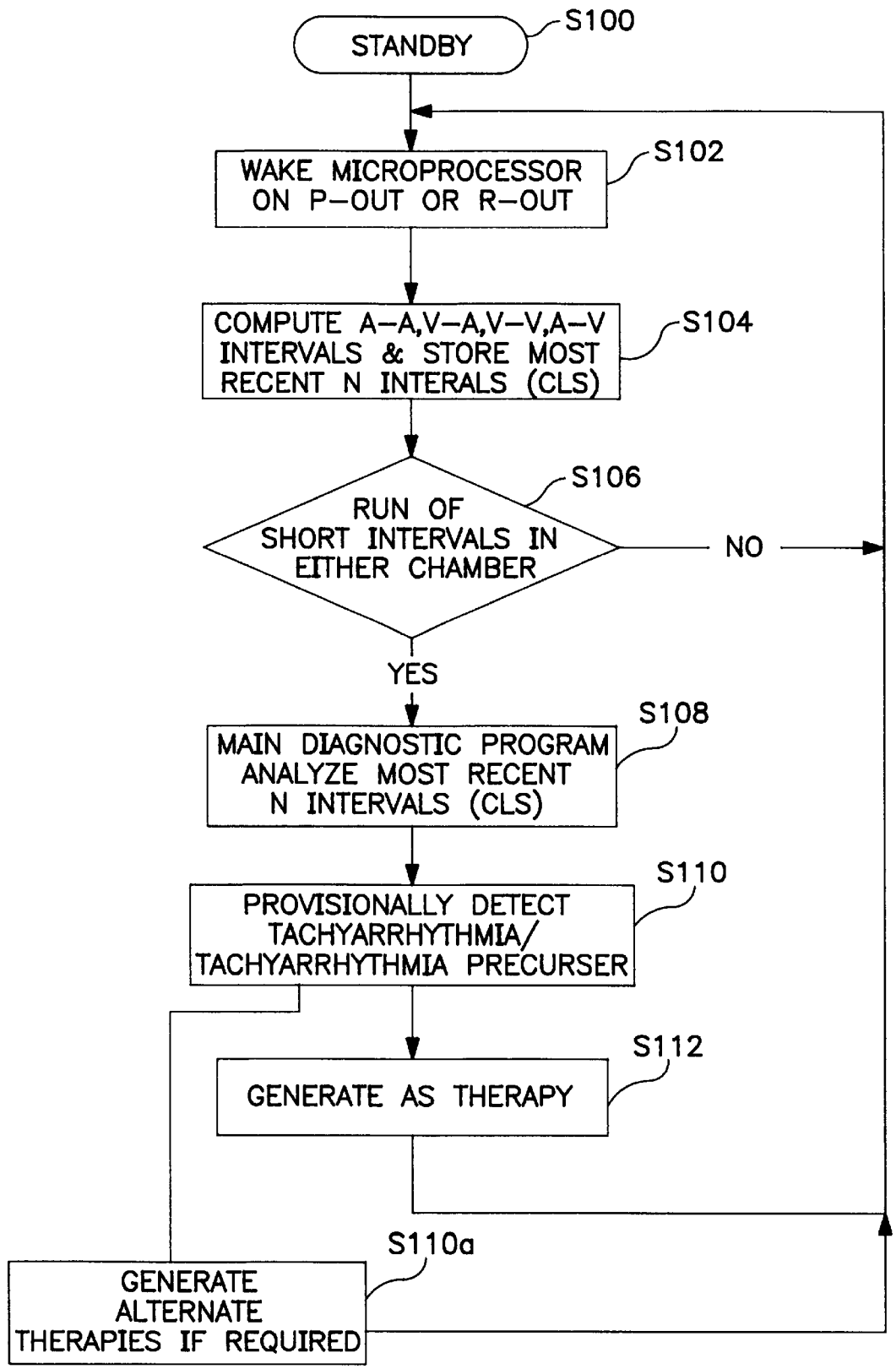
FIG. 4 is a flowchart illustrating overall steps of a first preferred embodiment of the method of practicing the present invention in countering the onset of a tachyarrhythmia indicated by an arrhythmic precursor or in response to a confirmed tachyarrhythmia episode usable in the system of FIGS. 2 and 3, and sub-systems thereof.

Turning to FIG. 4, it depicts the overall method of operation of the system of FIG. 3 in the context of the determination of the occurrence of a tachyarrhythmia or a precursor to a tachyarrhythmia episode. It should be noted that there are numerous tachy condition and event detection methods and programs known and used by others and there will be more developed in the future any of which would suffice for use with this invention, but I illustrate this one with particularity to complete the disclosure requirements only. At step S100, the microprocessor 224 is in the standby mode to conserve battery power. It will be assumed that a run of high rate atrial depolarizations are occurring such that bradycardia pacing modes (if available in the system) are suppressed in both chambers. As in the bradycardia operating modes, when an atrial or ventricular sense event interrupt (P-OUT or R-OUT) is received from the respective sense amplifier, the microprocessor 224 awakens in step S102 to compute and store the V-A, and A-A intervals or the V-V and AV intervals, respectively. The most recent series of intervals, extending over the preceding several minutes are stored in memory on a FIFO basis, as depicted in step S104, (although other methods for keeping intervals are well known and would, of course, be acceptable fro application to this invention). In the event that a predetermined number of short intervals less than an atrial or ventricular tachycardia detection interval (TDI) or fibrillation detection interval (FDI) occurs during a predetermined time interval or a preceding series of heart cycles, or other criteria, e.g., instability in a series of such intervals, are satisfied, the "run of short intervals" indication is provisionally determined as an abnormal cardiac rhythm at step S106. The main diagnostic routine for determining the type of tachyarrhythmia employing the rate, onset and stability criteria described above is then entered in step S108. The main diagnostic routine determines if the run of short intervals constitutes an abnormal cardiac rhythm representing the onset of a tachyarrhythmia including a precurser to a tachyarrhythmia.

Preferably, a simple rate criteria or sudden change in the stability of the rate may be used to provisionally confirm a tachyarrhythmia or tachyarrhythmia precurser in step S110. After such confirmation, the AS pulses is triggered and applied to the selected AS delivery electrodes in step S112. Preferably the AS pulse waveform is allowed to continue through the time of at least one cardiac cycle and up to several when tachyarrhythmia is possible or detected. This could be done using time periods between depolarizations that are sensed or pacing spikes, or even could be left on continuously. Alternatively all these alternative methods could be tried before applying a cardioversion therapy shock. While the AS pulses is delivered, the main operating program of FIG. 4 continues to process P-OUT and R-OUT signals to determine if the tachyarrhythmia is halted, continues or progresses to satisfy detection criteria for a more serious arrhythmia. In the latter case, the delivery of the AS pulses is halted and the AS generator 280 output terminals are isolated prior to the delivery of an anti-tachycardia pacing therapy or a cardioversion shock therapy(step 110a).

The timing diagram of FIG. 5A illustrates a variation on the first embodiment of the invention wherein the delivery of the AS pulses to the AS delivery electrodes about the heart is in a timed AS delivery interval after expiration of an AS delay interval timed from a sensed or paced event (shown in tracings (a)–(e)) as well as alternative pulse waveforms of the AS program that may be employed in all embodiments of the invention (tracings (f)–(i)).

Turning first to the illustrated pulse waveforms of tracings (f)–(i), the AS pulses are intended to be sub-threshold in nature, that is, of insufficient energy to depolarize the myocardial cells and/or shaped to avoid depolarizing the myocardial cells due to make or break excitation effects. Consequently, the delivery of these AS pulses presents issues including how to distribute the sub-threshold energy to an appreciable mass of myocardial cells to supress abberant electrical activity and to facilitate relaxation and refilling of the chamber with blood both without causing depolarization to occur or triggering an arrhythmia. In the context of an ICD or PCD of the type shown in FIGS. 2 and 3, the large surface area cardioversion electrodes and the pace/sense electrodes distributed about the heart may be optimally employed to distribute the AS pulses. The AS program of pulses or pulse waveforms may be delivered in the form of a single anodal pulse of constant amplitude as shown in tracing (i) or as a burst of such constant energy stimulation pulses. With respect to avoidance of leading or trailing edge effect excitation leading to depolarization of myocardial cells, the leading and/or trailing edges of the AS pulse or pulses of tracings (f)–(i) preferably have ramped amplitudes. In tracings (f) and (g) the ramp up leading edge amplitudes of a sub-set of the pulses of the burst are shown increasing from an initial amplitude to a maximum amplitude. In tracings (f) and (h) the ramp down trailing edge amplitudes of a further sub-set of the pulses of the burst are shown decreasing from the maximum amplitude to a terminating amplitude. In tracing (i), the ramp up leading edge and ramp down trailing edge waveforms between the initial amplitude, the maximum amplitude and the terminating amplitude are shown in dotted lines.

Turning to the timing of delivery and alternative forms of the AS pulses illustrated in FIG. 5A, in accordance with this variation of the first embodiment, it is preferred that either a single anodal pulse or a burst or train of constant or variable frequency pulses may be delivered in an AS delivery time interval timed out in tracing (e) after time-out of an AS delay interval (tracing (d)) from a preceding ventricular sense or pace event (tracings (a) and (b)). This synchronization method is described below in greater detail with respect to FIG. 6. Ventricular events are chosen in order to time the delivery of the AS energy to the selected heart chamber or both heart chambers during the relaxation phase of the cardiac cycle, if possible as illustrated in FIG. 1. The ventricular sense or pace event detected in tracing (b) also triggers the timing out of an escape interval in tracing (c) which may be terminated by the sensing of a subsequent ventricular event (R-OUT), depending on the operating mode of the system. The first depicted sequence shows the full time-out of the escape interval in tracing (c) and the AS delay and delivery intervals in tracings (d) and (e). The AS delay and delivery intervals are set to be completed within the escape interval and may be derived as a function of an intrinsic V-V V-A escape interval derived by measuring and averaging intervals between intrinsic ventricular and/or atrial sense events. The AS delay interval delays delivery of the AS pulses or pulse waveforms until after expiration of an excitable phase of the heart which follows an intrinsic or pace evoked R-wave. The AS delivery interval is timed to time-out before the end of the previously derived V-V escape interval. It is anticipated that the first embodiment of the invention will be practiced in the context of the detection of an atrial arrhythmia, while ventricular depolarizations continue and the depicted synchronization and timing remains possible.

If this invention is applied through a non-PCD type device alternative electrode arrangements may be necessary and any that are currently known and could be adapted to provide distribution of the sub-threshold energy to an appreciable mass of myocardial could be used. See for example the concurrently filed application serial No. (P3446) for some alternative delivery electrode means, that application being incorporated herein by this reference.

The AS delivery interval is timed to time-out before the end of the previously derived V-V or V-A escape interval. If the invention were to be used in a purely atrial chamber device or to also have an atrial chamber hyperpolarization electrode system, the illustrated tracings of FIG. 5B should be used as a guide to implementation of this invention. Here the timing stems from the A-Sense (P-wave or A-Pace signal). If preferred, a signal other than A-A interval could be used, such as V-A interval if desired. Note that the tracing (f) of FIG. 5B can take on the same or similar characteristics to those illustrated in FIGS. 5A(f–i), if desirable.

In the first illustrated case In FIG. 5A, the escape interval terminates in response to the sensing of a P-wave after the time-out of the AS delivery interval. In the second illustrated case, at the right side of FIG. 5A, the premature sensing of a qualified sense event 3, in this case an R-wave 4, should be acted upon by the device to terminate the AS delivery time interval (thus eliminating the unused temporal portion 6 of AS delivery interval 7. This can be handled in various ways by the device, a typical pacemaker shrinking the escape interval as in area 5 although many techniques may be used as is known to those of skill in this art.). If a sense event occurs earlier during the time-out of the AS delay interval, then the timing should be reset to restart the AS delay interval for the next heart cycle. This same feature should be implemented in the atrium if one is using a hyperpolarization AS system in the atrium, but in such systems, the truncation should be based on a PAC rather than a PVC as just illustrated.

If the AS pulses are not having the desired effect, the system should be programmed to retry and adjust the characteristics of the AS pulse over time. Of course this should not be done when alternate therapy would be indicated such as defibrillation, but rather should be done as one would calibrate the effectiveness of any pulse delivery system. The characteristics available for adjustment include pulse width, pulse amplitude, slope of leading and trailing edges of the pulse or pulse train and the timing of delivery with respect to the particular chamber's last and/or next depolarization event. This last characteristic can be varied by varying the AS delay interval and/or the AS delivery interval. The other characteristics can be varied as is well known in the art.

Referring briefly to FIG. 5C, in which the concept of break excitation is illustrated, an anodal pulse waveform, tracing (b), can trigger a myocardial depolarization (QRS of tracing (a)). In the early literature on cardiac pacing it was recognized that a larger pulse energy was required for anodal pacing than for the now universally adopted cathodal pacing waveforms. Accordingly the hyperpolarization waveform may require more energy than a typical pacing pulse, so long as terminating it does not cause break excitation. When there is an excitation, sufficient to cause a chamber depolarization (again, here illustrated as the QRS complex in (a)), a sense signal (tracing c) could be generated. If determined by the timing of the sense that the anodal pulse may have caused the depolarization, adjustments to the AS pulse characteristics should be made. These adjustments should be made concurrently and possibly independently of adjustments based on QT interval or any other electrocardiographic or cardiac cycle indicators of tachyarrhythmia susceptability.

In FIG. 6, preferred timing and delivery steps of the first embodiment of the present invention practiced in step S112 of FIG. 4 are depicted in an example providing the delivery of the AS pulse during a ventricular escape interval determined by monitoring and averaging the V-V interval on a continuous basis. The steps of FIG. 6 to carry out the timing of delivery illustrated in tracings (a)–(e) of FIG. 5 may be followed in the case where the AS pulse is delivered to the atria or to the ventricles or to both the atria and ventricles as long as the ventricular rate or V-V escape interval is regular and below an upper rate limit beyond which the timing of delivery may become impractical.

Under such favorable circumstances, the steps of FIG. 6 may be employed for suppressing or treating atrial tachyarrhythmias without providing or generating atrial shock therapies. In these cases involving hyperpolarization of the atria to suppress or revert an atrial tachyarrhythmia, atrial sense events are analyzed in the steps of FIG. 4 to determine the tachyarrhythmia or tachyarrhythmia precurser, and the ventricular sense events are employed in the steps of FIG. 6 to effect the preferred synchronization. If the requisite ventricular sense event characteristics from which the AS delivery time interval can be timed are not present, then the atrial AS pulse may be delivered asynchronously simply following the steps of FIG. 4.

Similarly, the steps of FIG. 6 may be employed in response to the onset of or a precurser ventricular rate or instability indicator of a low rate ventricular tachycardia to deliver the AS pulse to the ventricular AS delivery electrodes and hyperpolarize the ventricles. In this case, the ventricular sense events are analyzed to determine the need for the AS pulse delivery, and the AS pulse or pulse waveforms is delivered in the AS delivery time interval. Again, if the requisite ventricular sense event characteristics from which the AS delivery time interval can be timed are not present, then the ventricular AS pulse or pulse waveforms may be delivered asynchronously simply following the steps of FIG. 4.

In step S200 of FIG. 6, the algorithm is started, and the V-EVENT (R-OUT) sense events are monitored in step S202. The R—OUTs that occur in step S204 are used in step S206 to calculate and update an average V-V escape interval and a corresponding AS delay and AS delivery interval to be used for that average V-V escape interval. The occurrence of a V-EVENT may also terminate any delivery of an AS pulse currently being delivered. In general, it would be expected that in a typical range of heart beat rates, the AS delay interval would be varied through a relatively narrow range, and the AS delivery interval would be shortened as the average V-V interval shortens and lengthened as the average V-V interval lengthens to a greater extent.

The AS delay interval is then started in step S208, and after it times out in step S210, the AS delivery timer is started in step S212, and the delivery of the AS pulse for the AS delivery interval is started in step S214. The pulse characteristics of the AS pulse or pulse waveform, including the maximum amplitude, the frequency of pulse train therapies and the ramp-up and ramp-down of the single pulse or pulse train amplitudes as shown in tracings (e)–(i) of FIG. 5 are all controlled during step S214 in accordance with AS pulse characteristic control signals supplied on bus 282 of FIG. 3 from an AS pulse characteristics register in PTC circuit 212. The timing characteristics of the AS pulse, including the AS delay interval and the AS delivery interval are controlled by timing signals delivered from the AS delivery and delay interval timers in PTC circuit 212. The pulse and timing characteristics are collectively referred to as AS pulse characteristics and are ultimately defined in microprocessor 224 from programmed-in base characteristic settings. These settings of AS pulse characteristics may optionally be optimized in accordance with the teachings of the above-referenced (P-3346) application. When the AS delivery timer times out in step S216, the delivery of the AS pulse is stopped in step S218.

In a variation of the first embodiment of the invention, the delivery of the AS pulses depicted in FIG. 5 may be delivered in the AS delivery interval in accordance with the steps of FIG. 6 at all times or in response to a further precurser in a preemptive treatment mode in patients whose hearts are susceptible to episodes of atrial or ventricular tachyarrhythmia in an effort to suppress the onset of a tachyarrhythmia episode.

Turning to the second embodiment of the invention, in a particular reactive treatment, the method and apparatus of the invention is incorporated into a cardioversion system for determining the existence of a tachyarrhythmia, e.g. atrial or ventricular fibrillation, and delivering a cardioversion therapy, e.g. a defibrillation or synchronized cardioversion shock, to the affected heart chamber through the large surface area cardioversion electrodes (at least one of which is in substantial contact with the heart chamber) after charging up of high voltage output capacitors. In the charging time period, the AS pulse is delivered at the large surface area cardioversion electrodes in an effort to convert the tachyarrhythmia and to reduce the cardioversion shock energy required if necessary to convert. Confirmation of the tachyarrhythmia is made following charging of the high voltage output capacitors to determine the need for the cardioversion shock energy.

FIG. 7 illustrates the operating steps of the second embodiment which may be practiced in the PCD system of FIGS. 2 and 3 alone or in conjunction with the first embodiment. Steps S300–S308 are the same as steps S108 of FIG. 4. Instep S310, fibrillation is determined employing known fibrillation detection criteria. As described above, if atrial fibrillation/flutter is determined to be present, and if the ventricular rate is adequate, the steps of the first embodiment are preferred, assuming that atrial cardioversion is not prescribed. This embodiment assumes that a cardioversion therapy is prescribed for treating atrial or ventricular fibril-lation. In step S312, the HVCH signal is applied to the HV charge circuit 236 in FIG. 3, and in step S314 the AS pulse is delivered during charge up of the high voltage output capacitors, preferably between the cardioversion electrodes and the CAN electrode. After charge-up is completed, the continued existence of the fibrillation is confirmed in step S316 by processing the signals received from the pace/sense electrodes in a manner known in the art. The AS pulse is discontinued, and the AS pulse output terminals are disconnected from the cardioversion electrode terminals in switch matrix and protection circuit 208 in step S318. Then, the cardioversion shock is delivered in step S320. The success or failure of the cardioversion shock is assessed in a manner known in the art, and the delivery of the AS pulse may be continued thereafter.

Other AS delivery electrodes usable in the various embodiments and variations of the invention include the endocardial and epicardial cardioversion and pace/sense electrodes of all types known in the art. It is preferable that the AS delivery electrodes contact the heart chamber endocardium or epicardium either at multiple sites or over substantial areas so that myocardial cells in contact with or in the vicinity of the electrodes become hyperpolarized due to the AS pulse. A variety of exemplary distributed electrodes have been disclosed in the prior art for distributing electrodes against the endocardial surface of a heart chamber that may also be used to deliver the AS pulses over a wide area of the heart. For example, the distributed electrode systems disclosed in U.S. Pat. No. 5,181,111 and in commonly assigned co-pending U.S. patent application Ser. No. 08/587,699 filed Jan. 17, 1996, Williams et al., for MULTI-ELECTRODE, UNIFORM FIELD, INTRACARDIAC DEFIBRILLATION LEADS, both incorporated herein by reference, may be advantageously employed in the practice of the present invention. Similarly, epicardial patch cardioversion electrodes of the types shown in U.S. Pat. Nos. 4,821,723, 5,087,243 and 5,243,978, incorporated herein by reference, may be employed in either atrial and/or ventricular locations. Other large surface area endocardial cardioversion electrodes are disclosed, for example, in U.S. Pat. Nos. 5,433,729 and 5,509,925, and U.S. patent application Ser. No. 08/263,769 above referenced and, all incorporated herein by reference. Further exemplary AS delivery electrodes that may be employed in the practice of the invention are depicted and described in the above-referenced (P-3446) application.

While the determination of a precurser to or onset of a tachyarrhythmia has been described above in FIG. 4 in relation to the detection and analysis of sense events emanating from the heart chamber to be treated with the AS pulse, it will be understood that a wide variety of methods and apparatus may be employed to determine that the heart chamber is susceptible to the onset of the tachyarrhythmia, including that it exhibits a precursor of a tachyarrhythmia. For example, the determination may involve measuring other parameters alone or in conjunction with the analysis of atrial and/or ventricular sense events. Such other parameters that have been employed in determining a tachyarrhythmia onset or act as a leading indication or precursor may include signal levels or changes therein of signals related to or derived from transducers measuring blood pressure, blood gas, cardiac impedance, blood temperature, etc.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

What is claimed is:

1. A method of operation of an implantable medical device for managing tachyarrhythmias employing anodal stimulation comprising the steps of:

determining an anodal stimulation pulse delivery interval;

generating an anodal stimulation pulse having characteristics sufficient to hyperpolarize myocardial cells of the heart and insufficient to elicit depolarization of the myocardial cells; and delivering the anodal stimulation pulse to the heart during the anodal stimulation delivery interval.

2. The method of claim 1 wherein said device first determines a heart's susceptability to arrhythmia.

3. The method of claim 1 wherein said device first senses an arrhythmia before determining said anodal stimulation pulse delivery interval.

4. The method of claim 1 wherein said timing step further comprises the step of:

providing a sense signal in response to depolarizations of the patient's heart; and establishing an anodal stimulation delay interval between a sense signal and the commencement of the anodal stimulation delivery interval to ensure application of the anodal stimulation therapy during the intrinsic relaxation time between depolarizations of the cardiac cells of the heart.

5. The method of claim 1 wherein said generating step further comprises the step of:

establishing an anodal stimulation therapy pulse waveform comprising a plurality of anodal energy pulses commencing with an initial pulse having an initial pulse energy and terminating with a terminating pulse having a terminating pulse energy, and having intervening pulses of intervening energies such that a waveform is maintained from said initial to said terminating pulse and wherein the energy levels of these three types of pulses is predetermined or adjustable.

6. In an implantable pulse generator and lead system for providing cardioversion shocks through cardioversion electrodes to a chamber of a patient's heart to cardiovert a tachyarrhythmia episode, a method of hyperpolarizing myocardial cells of the heart chamber employing anodal stimulation comprising the steps of:

detecting depolarizations of a chamber of a patient's heart susceptible to a tachyarrhythmia and providing a sense signal in response thereto;

determining the existence of an abnormal cardiac rhythm requiring delivery of a cardioversion shock from a series of such sense signals;

commencing the charging of high voltage output capacitors of the implantable pulse generator to a cardioversion shock energy level;

generating an anodal stimulation therapy having characteristics sufficient to hyperpolarize myocardial cells of the heart chamber; and delivering the anodal stimulation therapy through the cardioversion electrodes to the heart chamber during the charging of the high voltage output capacitors.

7. The method of claim 6 further comprising the steps of:

terminating the anodal stimulation therapy prior to delivery of the cardioversion shock;

confirming the presence of the tachyarrhythmia prior to delivery of the cardioversion shock; and delivering the cardioversion shock through the cardioversion electrodes upon charging of the high voltage output capacitors to the cardioversion shock energy level and upon confirmation of the presence of the tachyarrhythmia.

8. An implantable pulse generator and lead system for managing tachyarrhythmias employing anodal stimulation energy applied to a heart chamber susceptible to tachyarrhythmia episodes comprising:

means for determining an anodal stimulation therapy delivery interval;

means for generating an anodal stimulation therapy having characteristics sufficient to hyperpolarize myocardial cells of the heart and insufficient to elicit depolarization of the myocardial cells; and means for delivering the anodal stimulation therapy to the heart during the anodal stimulation delivery interval.

9. Apparatus as set forth in claim 8 and further comprising:

means for determining that a heart chamber is susceptible to the onset of a tachyarrhythmia.

10. Apparatus as set forth in claim 8 and further comprising:

means for sensing a heart chamber tachyarrhythmia.

11. The system of claim 8 wherein said timing means further comprises:

means for detecting depolarizations of a chamber of a patient's heart and providing a sense signal in response thereto;

means for establishing an anodal stimulation delay interval between the sense signal and the commencement of the anodal stimulation delivery interval to ensure application of the anodal stimulation therapy during the intrinsic relaxation time between depolarizations of the cardiac cells of the heart.

12. The system of claim 8 wherein said generating means further comprises:

means for establishing an anodal stimulation therapy pulse waveform comprising a plurality of anodal energy pulses of differable energy values.

13. In an implantable pulse generator and lead system for providing cardioversion shocks through cardioversion electrodes to a chamber of a patient's heart to cardiovert a tachyarrhythmia episode, apparatus for hyperpolarizing myocardial cells of the heart chamber employing anodal stimulation energy comprising:

means for detecting depolarizations of a chamber of a patient's heart susceptible to a tachyarrhythmia and providing a sense signal in response thereto;

means for determining the existence of an abnormal cardiac rhythm requiring delivery of a cardioversion shock from a series of such sense signals;

means for commencing the charging of high voltage output capacitors of the implantable pulse generator to a cardioversion shock energy level;

means for generating an anodal stimulation therapy having characteristics sufficient to hyperpolarize myocardial cells of the heart chamber; and means for delivering the anodal stimulation therapy through the cardioversion electrodes to the heart chamber during the charging of the high voltage output capacitors.

14. The system of claim 13 further comprising:

means for terminating the anodal stimulation therapy prior to delivery of the cardioversion shock;

means for confirming the presence of the tachyarrhythmia prior to delivery of the cardioversion shock; and means for delivering the cardioversion shock through the cardioversion electrodes upon charging of the high voltage output capacitors to the cardioversion shock energy level and upon confirmation of the presence of the tachyarrhythmia.

15. An implantable pulse generator and lead system for managing atrial tachyarrhythmias employing anodal stimulation applied to atria susceptible to tachyarrhythmia episodes comprising:

means for detecting atrial depolarizations of a patient's atria susceptible to an atrial tachyarrhythmia and providing an atrial sense signal in response thereto;

means for detecting ventricular depolarizations of a patient's ventricle and providing a ventricular sense signal in response thereto;

means for determining an abnormal precursor cardiac rhythm representing the onset of an atrial tachyarrhythmia from one or more atrial sense signals;

means for determining an anodal stimulation therapy delivery interval;

means for generating an anodal stimulation therapy having characteristics sufficient to hyperpolarize atrial myocardial cells of the heart and insufficient to elicit depolarization of the myocardial cells; and means for delivering the anodal stimulation therapy to the atria during the anodal stimulation delivery interval.

16. The system of claim 15 wherein said means for determining an anodal stimulation therapy delivery interval further comprises:

means for establishing a delay interval between the atrial sense signal and the commencement of the anodal stimulation delivery interval to ensure application of the anodal stimulation therapy during the intrinsic relaxation time between depolarizations of the atrial cardiac cells of the heart.

17. The method of claim 1 and further comprising the steps:

measuring a physiologic parameter related to a change in said tachyarrhythmia, and adjusting the anodal stimulation characteristics responsive to said changes in said measure.

18. The system of claim 8 further comprising;

means to determine a measure of a physiologic parameter, and means to adjust characteristics of the anodal stimulation responsive to said measure.

* * * * *